(12) United States Patent
Pugin et al.

(10) Patent No.: US 8,450,501 B2
(45) Date of Patent: May 28, 2013

(54) BIDENTATE CHIRAL LIGANDS FOR USE IN CATALYTIC ASYMMETRIC ADDITION REACTIONS

(75) Inventors: Benoît Pugin, Münchenstein (CH); Matthias Lotz, Basel (CH); Heidi Landert, Bourrignon (CH); Adrian Wyss, Aesch (CH); Raphael Aardoom, Wallisellen (CH); Björn Gschwend, Zeiningen (CH); Andreas Pfaltz, Binningen (CH); Felix Spindler, Starrkirch-Wil (CH)

(73) Assignee: Solvias AG, Basel (CH)

( * ) Notice: Subject to any disclaimer, the term of this patent is extended or adjusted under 35 U.S.C. 154(b) by 212 days.

(21) Appl. No.: 12/734,696

(22) PCT Filed: Nov. 14, 2008

(86) PCT No.: PCT/EP2008/065607
§ 371 (c)(1),
(2), (4) Date: May 18, 2010

(87) PCT Pub. No.: WO2009/065784
PCT Pub. Date: May 28, 2009

(65) Prior Publication Data
US 2011/0118482 A1 May 19, 2011

(30) Foreign Application Priority Data
Nov. 20, 2007 (CH) ...................................... 1789/07

(51) Int. Cl.
*C07D 333/26* (2006.01)
(52) U.S. Cl.
USPC ............................................................ 549/6
(58) Field of Classification Search
USPC .................................................... 549/216, 6
See application file for complete search history.

(56) References Cited

U.S. PATENT DOCUMENTS

| 2008/0193357 A1 | 8/2008 | Scriban et al. |
| 2009/0082581 A1 | 3/2009 | Pugin et al. |

FOREIGN PATENT DOCUMENTS

| CA | 2 606 654 | 11/2006 |
| WO | 2007/016264 | 2/2007 |

OTHER PUBLICATIONS

International Search Report issued Apr. 17, 2009 in International (PCT) Application No. PCT/EP2008/065607.
Written Opinion issued Apr. 17, 2009 in International (PCT) Application No. PCT/EP2008/065607.
H. Brunner et al., "Enantioselective Catalysis 113: New Menthylphosphane Ligands Differing in Steric and Electronic Properties", Synthesis, No. 1, pp. 45-55, 1998.
R.B. King et al., "Poly(tertiary phosphines and arsines). 17. Poly(tertiary phoiphines) Containing Terminal Neomenthyl Groups as Ligands in Asymmetric Homogeneous Hydrogenation Catalysts", Journal of Organic Chemistry, vol. 44, No. 18, pp. 3095-3100, Aug. 31, 1979.
Carolyn Fisher et al., "Asymmetric Homogeneous Hydrogenation with Phosphine-Rhodium Complexes Chiral Both at Phosphorus and Carbon", Tetrahedron Letters, vol. 29, pp. 2487-2490, 1977.
Wenjun Tang et al., "New Chiral Phosphorus Ligands for Enantioselective Hydrogenation", Chemical Reviews, vol. 103, pp. 3029-3069, 2003.

*Primary Examiner* — Taofiq A Solola
(74) *Attorney, Agent, or Firm* — Wenderoth, Lind & Ponack, L.L.P.

(57) ABSTRACT

Compounds of the formula (I), in the form of mixtures comprising predominantly one diastereomer or in the form of pure diastereomers, $Z_1$-Q-P*$R_0R_1$ (I) in which $Z_1$ is a C-bonded, secondary phosphine group —$P(R)_2$; in which R is in each case independently hydrocarbon radicals or heterohydrocarbon radicals, or $Z_1$ is the —P*$R_0R_1$ group; Q is a bivalent, achiral, aromatic base skeleton, a bivalent, achiral ferrocene base skeleton, an optionally substituted bivalent cycloalkane or heterocycloalkane skeleton, or a $C_1$-$C_4$-alkylene skeleton.

18 Claims, No Drawings

BIDENTATE CHIRAL LIGANDS FOR USE IN CATALYTIC ASYMMETRIC ADDITION REACTIONS

The present invention relates to optically enriched or optically pure chiral ligands with a bivalent, achiral, aromatic base skeleton, a bivalent, achiral ferrocene base skeleton, an optionally substituted bivalent cycloalkane or heterocycloalkane skeleton, or a $C_1$-$C_4$-alkylene skeleton, in which base skeletons a secondary phosphine group is bonded directly to a carbon atom, or, in the case of cyclic base skeletons, directly to a carbon atom or via a $C_1$-$C_4$-alkylene group, and in which base skeletons a P-chiral group —$PR_0R_1$ is bonded to a carbon atom such that the phosphorus atoms are linked via 1 to 7 atoms of a carbon chain optionally interrupted by heteroatoms from the group of O, S, N, Fe and Si, where $R_0$ is —OH or methyl and $R_1$ is a C-bonded chiral, optically enriched or optically pure cycloalkyl or heterocycloalkyl which has a stereogenic carbon atom at least in the α-position to the P—C bond; to metal complexes of these bidentate ligands with transition metals; and to the use of the metal complexes in asymmetric syntheses, particularly in hydrogenations with hydrogen of prochiral organic compounds which contain at least one carbon/carbon or carbon/heteroatom double bond.

Metal complexes with chiral ligands have been found to be valuable catalysts in asymmetric syntheses. Practical benefit is possessed by those metal complexes with which, as well as sufficient catalytic activity, a high stereoselectivity can also be achieved. Without these two properties, there can be no implementation in industrial processes for economic reasons.

It is to date still impossible to predict which metal complexes with which ligands under which reaction conditions with which unsaturated substrates will give rise to practically usable hydrogenation results with regard to the catalytic activity and stereoselectivity. A multitude of different bidentate ligands has therefore been provided, which may contain chelating groups with oxygen, sulphur, nitrogen and/or phosphorus atoms (see for example W. Teng, X. Zhang, Chem. Rev. 2003, 103, 3029-3069). Among these bidentate ligands, P^N and P^P ligands have frequently been found to be useful, particularly when the chelating groups are bonded to aromatics with atropisomerism (bisarenes and bisheteroarenes) or planar isomerism (metallocenes).

WO 00/21663 describes diphosphines with RHP(=O) groups bonded via carbon atoms to a base skeleton and secondary phosphine groups —$PR_aR_b$, which are proposed as ligands for transition metals to form catalytic compounds. WO 00/21663, however, does not mention any enantiomeric diphosphines for stereoselective catalysts. Therefore, no optically enriched or pure, chiral ligands for stereoselective catalysts are mentioned either.

Recently, a bidentate ligand of the formula A has been described [see thesis by Xiaobin Jiang with Prof. J. G. de Vries and Prof. B. L. Feringa, University of Groningen 29 Nov. 2004 (ISBN: 90-367-2144X), which is not mentioned in later publications by Xiaobin Jiang et al. in Org. Lett., 5 (2003) 1503-6 and Tetrahedron: Asymmetry, 15 (2004) 2223-9]. This ligand was prepared as a racemate and optically resolved by HPLC with a chiral column:

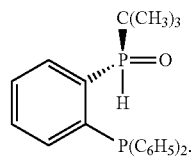

(A)

An enantiomeric ligand of the formula A has been used in an Rh complex in an equivalents ratio of 2:1 for the asymmetric hydrogenation of an enol carbamate (chapter 6, table 6.5, page 159), although only disappointing results have been found, i.e. low stereoselectivities and very low catalyst activities (TOF<1 $h^{-1}$). In the hydrogenation of an imine (chapter 5, page 120) with an Ir complex, only very low stereoselectivities and catalyst activities are achieved. The preparation of predominantly enantiomerically pure diphosphines is possible, but very inconvenient and uneconomic.

C. Fisher et al. describe, in Tetrahedron Letters 29, (1977) 2487-2490, a P-chiral monophosphine with a menthyl substituent, which is used as a ligand in rhodium complexes for hydrogenation, although achieved stereoselectivities (ee) up to 71% are considered to be too low.

H. Brunner et al. disclose, in Synthesis (1998) 45-55, diphosphine ligands with two dimenthylphosphine groups or one dimenthylphosphine and one diphenylphosphine group for enantioselective hydrogenations, but they enable stereoselectivities of only up to 30%.

G. Fries et al. describe, in Dalton Trans. (2004) 1873-1881, methylenediphosphines with a dimenthylphosphine group and a diisopropyl- or a diphenylphosphine group as ligands for rhodium complexes for enantioselective hydrogenation with optical yields up to 69% ee. These optical yields, however, still do not satisfy the demands of industrial processes.

R. B. King et al. describe, in J. of Org. Chem. 44(18) (1979) 3095-3100, 1-(menthyl)phenylphosphino-2-diphenylphosphinoethane as a ligand for homogeneous asymmetric hydrogenation with rhodium complexes. Optical yields of up to 85% are achieved. It is also mentioned that the P-chiral diphosphines with a stereogenic carbon atom in the α position to the P/C bond can be separated into the diastereomers by fractional crystallization.

It has now been found that, surprisingly, diphosphines with a P-chiral —$P(OH)R_1$ group and where $R_1$ is optically enriched or optically pure chiral α-substituted cycloalkyl or heterocycloalkyl can be separated easily into diastereomers and are therefore preparable in an economically viable manner. It has also been found that, surprisingly, diphosphines with a $P(OH)R_1$ group, in asymmetric hydrogenations with transition metal complexes, are notable for very high catalyst activities, and good to very high stereoselectivities can additionally often be achieved. It has also been found that, surprisingly, diphosphines with an achiral base skeleton and with two —$PR_0R_1$ groups or one —$PR_0R_1$ group and a secondary phosphine group, in asymmetric hydrogenations of unsaturated, prochiral compounds with metal complexes, as homogeneous catalysts, are notable for a high catalyst activity and improved stereoselectivity when $R_0$ is methyl.

The invention firstly provides compounds of the formula I, in the form of mixtures comprising predominantly one diastereomer or in the form of pure diastereomers, $$Z_1\text{-}Q\text{-}P^*R_0R_1 \qquad (I)$$

in which $Z_1$ is a C-bonded, secondary phosphine group —$P(R)_2$; in which R is in each case independently hydrocarbon radicals or heterohydrocarbon radicals, or $Z_1$ is the —$P^*R_0R_1$ group;

Q is a bivalent, achiral, aromatic base skeleton, a bivalent, achiral ferrocene base skeleton, an optionally substituted bivalent cycloalkane or heterocycloalkane skeleton, or a $C_1$-$C_4$-alkylene skeleton, and in which base skeletons a secondary phosphine group $Z_1$ is bonded directly to a carbon atom, or, in the case of cyclic base skeletons, directly to a carbon atom or via a $C_1$-$C_4$-alkylene group, and in which base skeletons a P-chiral group —$P^*R_0R_1$ is bonded directly to a carbon atom, or, in the case of cyclic base skeletons, directly to a carbon atom or via a $C_1$-$C_4$-alkylene group to a carbon atom such that the phosphorus atoms are linked via 1 to 7 atoms of a carbon chain optionally interrupted by heteroatoms from the group of O, S, N, Fe or Si;

$P^*$ is a chiral phosphorus atom;

$R_0$ is methyl or hydroxyl, preferably hydroxyl, and $R_0$ is methyl when $Z_1$ is the —$P^*R_0R_1$ group; and $R_1$ is a C-bonded optically enriched or optically pure chiral, mono- or polycyclic, nonaromatic hydrocarbon or heterohydrocarbon radical which has 3 to 12 ring atoms and 1 to 4 rings and which has a stereogenic carbon atom at least in the α position to the P—C bond.

By way of explanation, it should be noted that the compounds of the formula I also include the tautomeric forms in which the —$P^*(OH)R_1$ group is represented as —$P^*(=O)HR_1$. In the two tautomeric forms, the phosphorus atom is asymmetric and chiral.

In the context of the invention, "predominantly diastereomeric" means that, in mixtures, one diastereomer is present in an amount of at least 85% by weight, preferably at least 95% by weight and more preferably at least 97% by weight.

The carbon chain via which the phosphorus atoms are linked may be part of only a cyclic skeleton, or be part of a cyclic skeleton and unsubstituted or substituted alkylene groups bonded thereto. The carbon chain via which the phosphorus atoms are linked contains preferably 1 to 5 carbon atoms, or 1 to 4 carbon atoms and a heteroatom to form the —C—C—He—C—C sequence where He is O, S or $N(C_1$-$C_6$-alkyl). In a 1,1'-ferrocenediyl, the carbon chain interrupted by Fe, in a formal sense, has the —C—Fe—C— sequence. The carbon chain may be part of a ring, part of fused rings or part of linked rings (biphenylenes). In a particularly preferred embodiment, the phosphorus atoms are linked via a carbon chain having 1 to 4 carbon atoms or via the —C—Fe—C— group.

The secondary phosphine group $Z_1$ and the $PR_0R_1$ group may be bonded to a cyclic base skeleton either directly or via a bivalent $C_1$-$C_4$-carbon group. This bivalent group is preferably an alkylene group which is unsubstituted or substituted by $C_1$-$C_6$-alkyl (for example methyl, ethyl, n-propyl or n-butyl), $C_1$-$C_6$-alkoxy (for example methoxy, ethoxy, n-propoxy or n-butoxy), benzyl, benzyloxy, phenyl, phenyloxy, cyclopentyl, cyclopentyloxy, cyclohexyl, cyclohexyloxy, di($C_1$-$C_4$-alkyl)amino (for example dimethylamino and diethylamino), piperidinyl or morpholinyl and has 1 to 4 and preferably 1 or 2 carbon atoms. The alkylene group is preferably methylene or ethylene or corresponds to the formula —$CHR_8$— in which $R_8$ is $C_1$-$C_4$-alkyl, cyclohexyl or phenyl. The substitution of the $C_1$-$C_4$-alkylene group may lead to further asymmetric carbon atoms, such that the compounds of the formula I then have at least one further chiral centre. The $C_1$-$C_4$-alkylene group is preferably methylene, ethylene or $C_2$-$C_6$-alkylidene. Examples of alkylidene are ethylidene, 1,1-propylidene and 1,1-butylidene.

In a preferred embodiment, the secondary phosphine group $Z_1$ and the $PR_0R_1$ group are bonded to the base skeleton Q directly, via ethylene or a radical of the formula —$CHR_8$— in which $R_8$ is hydrogen, phenyl, methyl or ethyl. The secondary phosphine group and the $PR_0R_1$ group are more preferably bonded directly to cyclic radicals.

The bivalent, aromatic base skeleton Q does not contain an axial chiral centre or planar chiral centre. Substitutions on the aromatic base skeleton Q therefore must not lead to a bivalent base skeleton with an axial chiral centre or a planar chiral centre.

The Q group may be unsubstituted or, for example, mono- to hexasubstituted, preferably mono- to tetrasubstituted and more preferably mono- to disubstituted by substituents $R_x$ such as halogen, or a hydrocarbon radical which is inert under reaction conditions and is bonded via a carbon atom, oxygen atom, sulphur atom, nitrogen atom or silicon atom, where hydrocarbon radicals in the substituents $R_x$ may themselves be substituted. When the Q group is a cyclic radical, these radicals may also be provided with ring-forming substituents, for example $C_2$-$C_4$-alkylene, $C_2$-$C_4$-alkenylene, $C_4$-$C_8$-alkadienylene, $C_1$-$C_2$-alkylenediamino or $C_1$-$C_2$-alkylenedioxy. When at least two substituents in the Q group are bonded, they may be the same or different.

The optionally substituted substituent $R_x$ may, for example, be $C_1$-$C_{12}$-alkyl, preferably $C_1$-$C_8$-alkyl and more preferably $C_1$-$C_4$-alkyl. Examples are methyl, ethyl, n- or i-propyl, n-, i- or t-butyl, pentyl, hexyl, octyl, decyl, undecyl and dodecyl.

The optionally substituted substituent $R_x$ may, for example, be $C_5$-$C_8$-cycloalkyl, preferably $C_5$-$C_6$-cycloalkyl. Examples are cyclopentyl, cyclohexyl and cyclooctyl.

The optionally substituted substituent $R_x$ may, for example, be $C_5$-$C_8$-cycloalkylalkyl, preferably $C_5$-$C_6$-cycloalkylalkyl having, for example, 1 to 4 carbon atoms in the alkyl. Examples are cyclopentylmethyl, cyclohexylmethyl or -ethyl and cyclooctylmethyl.

The optionally substituted substituent $R_x$ may, for example, be $C_6$-$C_{18}$-aryl and preferably $C_6$-$C_{10}$-aryl. Examples are phenyl or naphthyl.

The optionally substituted substituent $R_x$ may, for example, be $C_7$-$C_{12}$-aralkyl, for example benzyl or 1-phenyleth-2-yl.

The optionally substituted substituent $R_x$ may, for example, be tri($C_1$-$C_4$-alkyl)Si or triphenylsilyl. Examples of trialkylsilyl are trimethyl-, triethyl-, tri-n-propyl-, tri-n-butyl- and dimethyl-t-butylsilyl.

The substituent $R_x$ may, for example, be halogen. Examples are F and Cl.

The optionally substituted substituent $R_x$ may, for example, be an alkoxy radical or thio radical of the formulae —$N(R_{05})_2$, —$OR_{05}$ and —$SR_{05}$, in which $R_{05}$ is $C_1$-$C_{12}$-alkyl, preferably $C_1$-$C_8$-alkyl and more preferably $C_1$-$C_4$-alkyl; $C_5$-$C_8$-cycloalkyl, preferably $C_5$-$C_6$-cycloalkyl; $C_6$-$C_{18}$-aryl and preferably $C_6$-$C_{10}$-aryl; or $C_7$-$C_{12}$-aralkyl. Examples of these hydrocarbon radicals have already been mentioned above for the substituents.

The hydrocarbon radicals of the substituents $R_x$ may in turn be mono- or polysubstituted, for example mono- to trisubstituted, preferably mono- or disubstituted, for example by halogen (F or Cl, particularly F), —$NR_{001}R_{002}$, $C_1$-$C_4$-alkyl, $C_1$-$C_4$-alkoxy, $C_1$-$C_4$-alkylthio, $C_5$-$C_6$-cycloalkyl, phenyl, benzyl, phenoxy or benzyloxy, where $R_{001}$ and $R_{002}$ are each independently $C_1$-$C_4$-alkyl, cyclopentyl, cyclohexyl, phenyl, benzyl, or $R_{001}$ and $R_{002}$ together are tetramethylene, pentamethylene or 3-oxapentane-1,5-diyl. The hydrocarbon radicals of the substituents $R_x$ are preferably unsubstituted.

Q is preferably unsubstituted or substituted by F, $CF_3$, Cl, $C_1$-$C_4$-alkyl, $C_1$-$C_4$-alkoxy, $C_1$-$C_4$-alkylthio, $(C_1$-$C_4$-alkyl$)_2$N or $(C_1$-$C_4$-alkyl$)_3$Si.

In a preferred embodiment, Q is
(a) bivalent arene or heteroarene, in particular 1,2-arene or a 1,2-heteroarene
(b) 1,1'-biaryl-2,2'-diyl, 1,1'-biheteroaryl-2,2'-diyl and 1,1'-arylheteroaryl-2,2'-diyl, each optionally attached via a bridging group,
(c) 1,1'-ferrocenylene;
(d) $C_4$-$C_8$-cycloalkylene-1,2- or 1,3-diyl or $C_3$-$C_7$-heterocycloalkylene-1,2- or 1,3-diyl with N, NH or N($C_1$-$C_4$-alkyl), O or S heteroatoms, or
(e) linear $C_1$-$C_4$-alkylene, where these radicals are unsubstituted or substituted, for example by halogen (F or Cl), $CF_3$, $(C_1$-$C_4$-alkyl$)_2$N, $C_1$-$C_4$-alkyl, $C_1$-$C_4$-alkoxy or a ring-forming alkylenedioxy group.

A bivalent, aromatic base skeleton may be a 1,2-arene or 1,2-heteroarene. This bivalent, aromatic base skeleton Q may be $C_6$-$C_{22}$-arylene or $C_2$-$C_{20}$-heteroarylene having one or more heteroatoms or heteroatomic groups selected from the group of —O—, —S—, —$NR_{06}$— and —N=, where $R_{06}$ is $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl, $C_6$-$C_{10}$-aryl-$C_1$-$C_4$-alkyl or a protecting group. Protecting groups are, for example, acyl, for example $C_1$-$C_8$-acyl or $C_1$-$C_8$-haloacyl derived from carboxylic acids or sulphonic acids, or N,N-di-$C_1$-$C_4$-alkylaminocarbonyl, for example dimethylaminocarbonyl. In the heteroarylene, at least 2 ring carbon atoms are bonded to one another. Heteroarylene contains preferably 5 or 6 ring atoms and preferably 1 to 3, more preferably 1 or 2 heteroatoms in the ring. Arylene and heteroarylene may be aromatic or aromatic-aliphatic, fused ring systems. Heteroarylene may contain a plurality of heteroatoms in the same or different rings of fused ring systems.

In a preferred configuration, the bivalent, aromatic base skeleton Q is $C_6$-$C_{14}$-arylene and more preferably $C_6$-$C_{10}$-arylene. Examples of arylene are 1,2-phenylene, 1,2-, 2,3- or 1,8-naphthylene, 1,2-, 2,3-, 4,5-, 5,6- or 9,10-phenanthrenylene, 1,2-, 2,3-anthracenylene, 1,2-, 2,3-naphthacenylene, 1,2- or 2,3-fluorenylene and 1,2- or 3,4-perylenylene. Particularly preferred arylene radicals are naphthylene and phenylene.

In another preferred configuration, the bivalent, aromatic base skeleton Q is $C_3$-$C_{14}$- and more preferably $C_4$-$C_{10}$-heteroarylene having one to three heteroatoms or heteroatomic groups selected from the group of —O—, —S—, —$NR_{06}$— or —N=, where $R_{06}$ is H, $C_1$-$C_4$-alkyl or a protecting group. Examples of heteroarylene are 1,2- or 2,3-furanylene, 1,2- or 2,3-thiophenylene, 1,2- or 2,3-pyrrolylene, 4,5-thiazolylene, 4,5-isoxazolylene, 4,5-pyrazolylene, 3,4- or 4,5-imidazolylene, 2,3- or 5,6-benzofuranylene, 2,3- or 5,6-benzthiophenylene, 2,3- or 5,6-indolylene, 2,3- or 3,4-pyridinylene, 4,5- or 5,5-pyrimidinylene, 3,4-pyridazinylene, 2,3-pyrazinylene, 2,3- or 5,6-quinolinylene, 3,4-isoquinolinylene and 2,3-quinoxalinylene. Preferred heteroarylenes are furanylene, thiophenylene, benzofuranylene and benzothiophenylene.

1,1'-Biaryl-2,2'-diyl, 1,1'-biheteroaryl-2,2'-diyl, 1,1'-arylheteroaryl-2,2'-diyl and bisaryls 1,1'-bonded via carbon atoms or heteroatoms are summarized hereinafter as 2,2'-biphenylenes.

A bivalent, aromatic base skeleton may be a 2,2'-biphenylene. These biphenylenes are aryl, heteroaryl or aryl and heteroaryl bonded in the 1,1'-positions, optionally via a bridging group $X_1$. Aryl and heteroaryl may also be fused ring systems. Aryl may be $C_6$-$C_{12}$-aryl (preferably naphthyl and more preferably phenyl), and heteroaryl may be $C_3$-$C_{11}$-heteroaryl having one or more heteroatoms or heteroatomic groups selected from the group of —O—, —S—, —$NR_{06}$— and —N=, where $R_{06}$ is H, $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl, $C_6$-$C_{10}$-aryl-$C_1$-$C_4$-alkyl or a protecting group. Protecting groups are, for example, acyl, for example $C_1$-$C_8$-acyl or $C_1$-$C_8$-haloacyl derived from carboxylic acids or sulphonic acids, or N,N-di-$C_1$-$C_4$-alkylaminocarbonyl, for example dimethylaminocarbonyl. The heteroaryl is preferably monocyclic, contains preferably 5 or 6 ring atoms and preferably 1 to 3, more preferably 1 or 2 heteroatoms in the ring. Examples of preferred heteroaryl are thiophenyl, furanyl, N-methylpyrrolinyl, benzothiophenyl, benzofuranyl and indolyl. The bridging group $X_1$ may be selected from —O—, —S—, —$NR_{07}$—, $C_1$-$C_2$-alkylene, $C_2$-$C_{18}$-alkylidene, $C_3$-$C_6$-cycloalkyl-1,2-ene or $C_3$-$C_6$-cycloalkylidene, —CH(O—$C_1$-$C_4$-alkyl)- and —Si($R_{07}$)$_2$—, where $R_{07}$ is H or $C_1$-$C_{12}$-alkyl, $C_5$- or $C_6$-cycloalkyl, $C_5$- or $C_6$-cycloalkylmethyl or -ethyl, phenyl, benzyl or 1-phenyleth-2-yl.

In a preferred embodiment the bivalent, aromatic base skeleton Q is 2,2'-biphenylene in which the two aryl, the two heteroaryl or aryl and heteroaryl in the 1,1' positions are linked directly or via a bridging group $X_1$, wherein $X_1$ is selected from —O—, —S—, —$NR_{07}$—, $C_1$-$C_2$-alkylene, $C_2$-$C_{18}$-alkylidene, $C_3$-$C_6$-cycloalkyl-1,2-ene or $C_3$-$C_6$-cycloalkylidene, —CH(O—$C_1$-$C_4$-alkyl)- and —Si($R_{07}$)$_2$—, where $R_{07}$ is H or $C_1$-$C_{12}$-alkyl, $C_5$- or $C_6$-cycloalkyl, $C_5$- or $C_6$-cycloalkylmethyl or -ethyl, phenyl, benzyl or 1-phenyleth-2-yl. Preferably aryl is $C_6$-$C_{12}$-aryl and heteroaryl is a $C_3$-$C_{11}$-heteroaryl having one or more heteroatoms or heteroatomic groups selected from the group of —O—, —S—, —$NR_{06}$— or —N=, where $R_{06}$ is $C_1$-$C_8$-alkyl, $C_3$-$C_8$-cycloalkyl, $C_3$-$C_8$-cycloalkyl-$C_1$-$C_4$-alkyl, $C_6$-$C_{10}$-aryl, $C_6$-$C_{10}$-aryl-$C_1$-$C_4$-alkyl or a protecting group, and the bridging group $X_1$ is —O— —S—, —$NR_{07}$—, $C_1$-$C_{18}$-alkylene, $C_2$-$C_{18}$-alkylidene, $C_3$-$C_{12}$-cycloalkylene or -cycloalkylidene, —CH(O—$C_1$-$C_4$-alkyl)-, —Si(O$R_{07}$)$_2$— or —Si($R_{07}$)$_2$—, where $R_{07}$ is $C_1$-$C_{12}$-alkyl, $C_5$- or $C_6$-cycloalkyl, $C_5$- or $C_6$-cycloalkylmethyl or -ethyl, phenyl, benzyl or 1-phenyleth-2-yl.

In a preferred embodiment, the 2,2'-biphenylene is phenyl or naphthdiyl bonded directly or via a bridging group $X_1$, where $X_1$ is —$CH_2$—, —$(CH_2)_2$—, $C_2$-$C_8$-alkylidene, cyclopentylidene, cyclohexylidene, —O—, —S—, —$NR_{07}$— or —Si($R_{07}$)$_2$—, and $R_{07}$ is $C_1$-$C_4$-alkyl, and where the two phenyls in the two other ortho positions may be bonded to methylene, ethylene, $C_2$-$C_8$-alkylidene, —O— or —($C_1$-$C_4$-alkyl)N—, to form a tricyclic system.

A bivalent, aromatic base skeleton may be a 1,1'-ferrocenylene of the formula

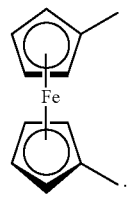

A bivalent base skeleton may be a 1,2- or 1,3-$C_3$-$C_{12}$-, preferably $C_4$ to $C_{10}$-cycloalkylene. They may be mono- or polycyclic radicals (fused ring systems having, for example, 2 to 4 rings). Some examples are 1,2-cyclopropylene, 1,2- or 1,3-cyclobutylene, 1,2- or 1,3-cyclopentylene, 1,2- or 1,3- cyclohexylene, 1,2- or 1,3-cycloheptylene, 1,2- or 1,3-cyclooctylene, 1,2- or 1,3-cyclononylene, 1,2- or 1,3-cyclodecylene, 1,2- or 1,3-cyclododecylene, [2,2,1]-bicycloheptane-1,2-diyl, [2,2,2]-bicyclooctane-2,3-diyl and tetralin-3,4-diyl.

A bivalent base skeleton may be a 1,2- or -1,3-$C_2$-$C_{11}$-, preferably $C_3$-$C_9$-heterocycloalkylene, in which at least 2 linked carbon atoms are present in the ring. The heteroatoms may be selected from the group of —O—, —S—, —N-benzyl-, —N═ and —N(C1-C4-alkyl)-. They may be mono- or polycyclic radicals (fused ring systems having, for example, 2 to 4 rings). Some examples are pyrrolidine-2,3- or -3,4-diyl, tetrahydrofuran-2,3- or -3,4-diyl, tetrahydrothiophene-2,3- or -3,4-diyl, piperidine-2,3- or -3,4-diyl and tetrahydropyran-2,3- or -3,4-diyl.

A bivalent base skeleton may be an unsubstituted or $C_1$-$C_4$-alkyl- or phenyl-substituted $C_1$-$C_4$-alkylene. Preference is given to unsubstituted methylene and ethylene. Some examples are methylene, ethylene, 1,2- or 1,3-propylene, 1,2-, 1,3- or 1,4-butylene, ethylidene, 1,1- or 2,2-propylidene, and 1,1- or 2,2-butylidene.

The hydrocarbon radicals and heterohydrocarbon radicals as substituents in the secondary phosphine group $Z_1$ may be unsubstituted or substituted and contain heteroatoms selected from the group of O, S, —N═ and N($C_1$-$C_4$-alkyl). They may contain 1 to 30, preferably 1 to 20, and more preferably 1 to 12 carbon atoms. The hydrocarbon radical may be selected from the group of linear or branched $C_1$-$C_{18}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl or benzyl; or halogen-, $C_1$-$C_6$-alkyl-, trifluoromethyl-, $C_1$-$C_6$-alkoxy-, trifluoromethoxy-, $(C_6H_5)_3Si$—, $(C_1$-$C_{12}$-alkyl$)_3$Si—, or secondary amino-substituted phenyl, naphthyl, furyl or benzyl.

Examples of phosphorus substituents as alkyl which preferably contains 1 to 6 carbon atoms are methyl, ethyl, n-propyl, i-propyl, n-butyl, i-butyl, t-butyl, and the isomers of pentyl and hexyl. Examples of phosphorus substituents as optionally alkyl-substituted cycloalkyl are cyclopentyl, cyclohexyl, methyl- and ethylcyclohexyl, and dimethylcyclohexyl. Examples of phosphorus substituents as alkyl- and alkoxy-substituted phenyl and benzyl are methylphenyl, dimethylphenyl, trimethylphenyl, ethylphenyl, methylbenzyl, methoxyphenyl, dimethoxyphenyl, trimethoxyphenyl, trifluoromethylphenyl, bis(trifluoromethyl)phenyl, tris(trifluoromethyl)phenyl, trifluoromethoxyphenyl, bis(trifluoromethoxy)phenyl, fluoro- and chlorophenyl and 3,5-dimethyl-4-methoxyphenyl.

Preferred secondary phosphine groups are those which contain radicals selected from the group of $C_1$-$C_6$-alkyl, unsubstituted or mono- to tri-$C_1$-$C_4$-alkyl- or —$C_1$-$C_4$-alkoxy-substituted cyclopentyl, cyclohexyl, norbornyl or adamantyl, benzyl and particularly phenyl which is unsubstituted or substituted by 1 to 3 $C_1$-$C_4$-alkyl, $C_1$-$C_4$-alkoxy, $C_1$-$C_4$-fluoroalkyl or $C_1$-$C_4$-fluoroalkoxy, F and Cl.

The secondary phosphine group corresponds preferably to the formula —$PR_2R_3$ in which $R_2$ and $R_3$ are each independently a hydrocarbon radical or an O-atom(s) containing heterohydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$amino, $(C_6H_5)_3Si$, $(C_1$-$C_{12}$-alkyl$)_3$Si, halogen.

Preferably, $R_2$ and $R_3$ are radicals selected from the group of linear and branched $C_1$-$C_6$-alkyl, unsubstituted or mono- to tri-$C_1$-$C_4$-alkyl- or —$C_1$-$C_4$-alkoxy-substituted cyclopentyl or cyclohexyl, norbornyl, adamantyl, furyl, unsubstituted or mono- to tri-$C_1$-$C_4$-alkyl- or —$C_1$-$C_4$-alkoxy-substituted benzyl, and especially unsubstituted or mono- to tri-F—, —Cl—, —$C_1$-$C_4$-alkyl-, —$C_1$-$C_4$-alkoxy-, —$C_1$-$C_4$-fluoroalkyl- or —$C_1$-$C_4$-fluoroalkoxy-substituted phenyl.

More preferably, $R_2$ and $R_3$ are radicals selected from the group of $C_1$-$C_6$-alkyl, cyclopentyl, cyclohexyl, furyl, and unsubstituted or mono- to tri-F—, —Cl—, —$C_1$-$C_4$-alkyl-, —$C_1$-$C_4$-alkoxy- and/or —$C_1$-$C_4$-fluoroalkyl-substituted phenyl.

When $R_2$ and $R_3$ in the —$PR_2R_3$ group are different, the phosphorus atom of the secondary phosphine group has a chiral centre. $R_2$ and $R_3$ are preferably identical radicals.

The secondary phosphine group may be cyclic secondary phosphino, for example those of the formulae

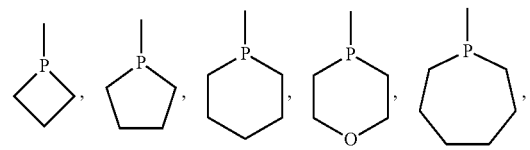

which are unsubstituted or mono- or polysubstituted by $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy, or $C_1$-$C_4$-alkylidenedioxy.

The substituents may be bonded in one or both a positions to the phosphorus atom, in order to introduce chiral carbon atoms. The substituents in one or both α positions are preferably $C_1$-$C_4$-alkyl or benzyl, for example methyl, ethyl, n- or i-propyl, benzyl or —$CH_2$—O—$C_1$-$C_4$-alkyl or —$CH_2$—O—$C_6$-$C_{10}$-aryl.

Substituents in the β,γ positions may, for example, be $C_1$-$C_4$-alkyl, $C_1$-$C_4$-alkoxy, benzyloxy, or —O—$CH_2$—O—, —O—CH($C_1$-$C_4$-alkyl)-O—, and —O—C($C_1$-$C_4$-alkyl$)_2$—O—. A few examples are methyl, ethyl, methoxy, ethoxy, —O—CH(methyl)-O—, and —O—C(methyl$)_2$-O—.

According to the type of substitution and number of substituents, cyclic phosphine radicals may be C-chiral, P-chiral or C- and P-chiral.

An aliphatic 5- or 6-membered ring or benzene may be fused to two adjacent carbon atoms in the radicals of the above formulae.

The cyclic secondary phosphino may, for example, correspond to the formulae (only one of the possible diastereomers is specified)

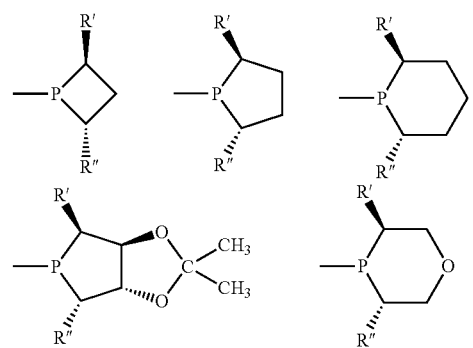

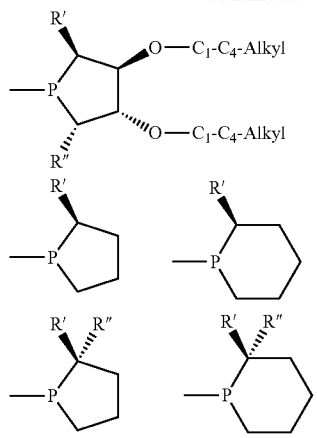

in which the R' and R'' radicals are each $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R'' are identical or different from one another.

In the compounds of the formula I, secondary phosphine is preferably an acyclic secondary phosphine selected from the group of —P($C_1$-$C_6$-alkyl)$_2$, —P($C_5$-$C_8$-cycloalkyl)$_2$, —P($C_7$-$C_8$-bicycloalkyl)$_2$, —P(o-furyl)$_2$, —P($C_6H_5$)$_2$, —P[2-($C_1$-$C_6$-alkyl)$C_6H_4$]$_2$, —P[3-($C_1$-$C_6$-alkyl)$C_6H_4$]$_2$, —P[4-($C_1$-$C_6$-alkyl)$C_6H_4$]$_2$, —P[2-($C_1$-$C_6$-alkoxy)$C_6H_4$]$_2$, —P[3-($C_1$-$C_6$-alkoxy)$C_6H_4$]$_2$, —P[4-($C_1$-$C_6$-alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)-$C_6H_3$]$_2$, —P[3,5-bis($C_1$-$C_6$-alkyl)$_2C_6H_3$]$_2$, —P[3,5-bis($C_1$-$C_6$-alkoxy)$_2C_6H_3$]$_2$, and —P[3,5-bis($C_1$-$C_6$-alkyl)$_2$-4-($C_1$-$C_6$-alkoxy)$C_6H_2$]$_2$, or a cyclic phosphine selected from the group of

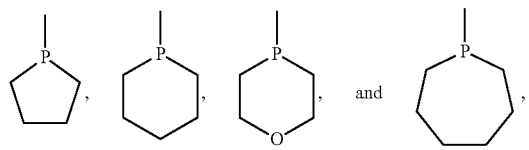

which are unsubstituted or mono- or polysubstituted by $C_1$-$C_4$-alkyl, $C_1$-$C_4$-alkoxy, $C_1$-$C_4$-alkoxy-$C_1$-$C_2$-alkyl, phenyl, benzyl, benzyloxy, or $C_1$-$C_4$-alkylidenedioxy.

A few specific examples are —P($CH_3$)$_2$, —P(i-$C_3H_7$)$_2$, —P(n-$C_4H_9$)$_2$, —P(i-$C_4H_9$)$_2$, —P(t-$C_4H_9$)$_2$, —P($C_5H_9$), —P($C_6H_{11}$)$_2$, —P(norbornyl)$_2$, —P(o-furyl)$_2$, —P($C_6H_5$)$_2$, P[2-(methyl)-$C_6H_4$]$_2$, P[3-(methyl)$C_6H_4$]$_2$, —P[4-(methyl)$C_6H_4$]$_2$, —P[2-(methoxy)$C_6H_4$]$_2$, —P[3-(methoxy)$C_6H_4$]$_2$, —P[4-(methoxy)$C_6H_4$]$_2$, —P[3-(trifluoromethyl)$C_6H_4$]$_2$, —P[4-(trifluoromethyl)-$C_6H_4$]$_2$, —P[3,5-bis(trifluoromethyl)$C_6H_3$]$_2$, —P[3,5-bis(methyl)$_2C_6H_3$]$_2$, —P[3,5-bis(methoxy)$_2C_6H_3$]$_2$, and —P[3,5-bis(methyl)$_2$-4-(methoxy)$C_6H_2$]$_2$, and those of the formulae

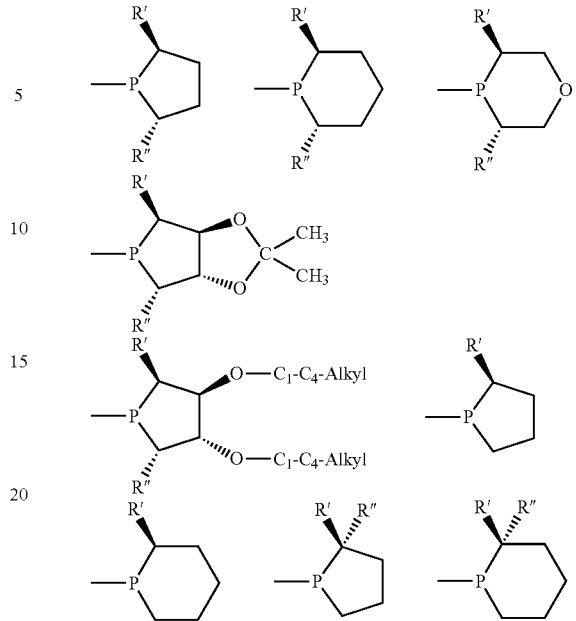

in which
R' is methyl, ethyl, methoxy, ethoxy, phenoxy, benzyloxy, methoxymethyl, ethoxymethyl or benzyloxymethyl, and R'' is independently as defined for R', and is different from R'.

$R_1$ as an optically enriched or optically pure, chiral, polycyclic, nonaromatic hydrocarbon or heterohydrocarbon radical, may, for example, be fused ring systems, bridged ring systems or fused and bridged ring systems. Mono- and polycyclic radicals $R_1$ contain, with the phosphorus atom, a structural element of the formula

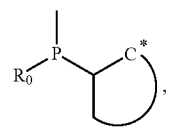

in which C* is the stereogenic α-carbon atom which bears a substituent or is part of a polycycle and the "arc" with the bonds represents a mono- or polycyclic radical.

Heteroatoms may be selected from the group of O, S, N and N($C_1$-$C_4$-alkyl).

The stereogenic α-carbon atom in the $R_1$ radical may be formed by substituents such as $C_1$-$C_6$-alkyl, $C_1$-$C_6$-alkoxy, $C_5$-$C_6$-cycloalkyl or $C_1$-$C_6$-alkoxy-$C_1$-$C_4$-alkyl, and preferably $C_1$-$C_4$-alkyl, $C_1$-$C_4$-alkoxy, $C_5$-$C_6$-cycloalkyl or $C_1$-$C_4$-alkoxymethyl. $R_1$ may, in the second α position and/or other positions, contain further substituents, for example $C_1$-$C_4$-alkyl, $C_1$-$C_4$-alkoxy, $C_5$-$C_6$-cycloalkyl or $C_1$-$C_4$-alkoxymethyl. The stereogenic α-carbon atom in the $R_1$ radical may also be formed by a fused-on, nonaromatic ring. In addition, an aromatic may be fused onto cyclic radicals.

The $R_1$ radical may contain one or more further stereogenic carbon atoms.

$R_1$ is preferably cycloalkyl, cycloalkenyl, heterocyclyl or heterocyclenyl having preferably 3 to 10 and more preferably 4 to 7 ring atoms, and also 1 to 4 rings. $R_1$ is most preferably cycloalkyl, cycloalkenyl, polycycloalkyl or polycycloalkenyl having 2 to 4 rings and having 4 to 7 carbon atoms in the rings.

Some examples of heterocyclyl are tetrahydrofuranyl and -thiophenyl, N-methylpyrrolidinyl, piperidinyl, dihydrothiophene, dihydrobenzofuran and dihydroindole.

$R_1$ may, as cycloalkyl and polycycloalkyl, derive, for example, from cyclopropane, cyclobutane, cyclopentane, cyclohexane, cycloheptane, cyclooctane, decalin, hydrindane, tetrahydronaphthalene, dihydroindane, [2,2,1]-bicycloheptane (norbornane), [2,2,2]-bicyclooctane, [2,2,1]-7-methylbicycloheptane, [2,2,1]-7,7-dimethylbicycloheptane and [2,2,1]-7-oxabicycloheptane.

In a preferred embodiment, $R_1$ derives from optically pure or highly enriched, chiral terpene alcohols (removal of the OH group), which are preparable and purchasable economically. Examples are menthol, neomenthol, norborneol, borneol, camphenol, isopinocampheol and carveol.

Particularly preferred "terpene radicals" are both enantiomers of menthyl, neomenthyl, bornyl and isopinocamphyl of the formulae

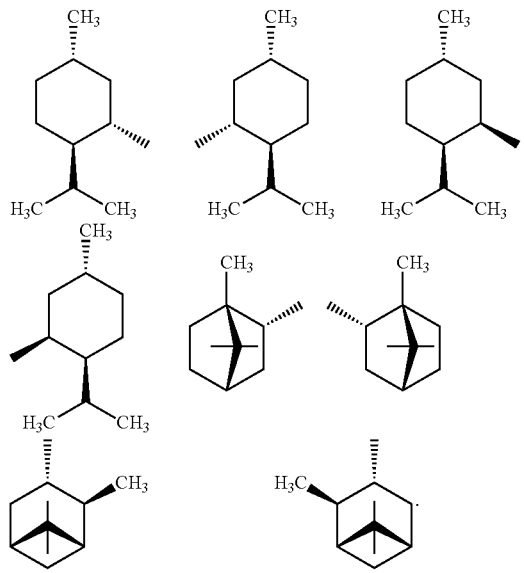

A preferred subgroup of inventive compounds of the formula I is that of those in which Q when defined as arene or heteroarene is an unsubstituted radical, or one substituted as detailed above, of the formulae

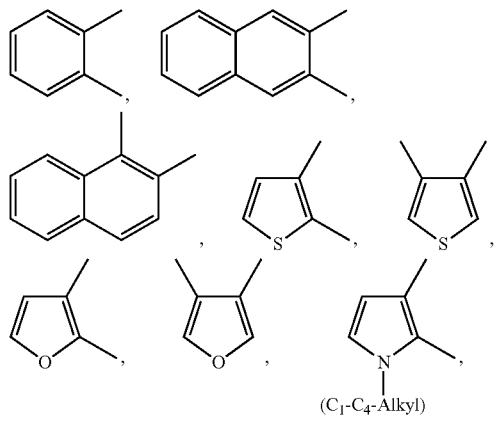

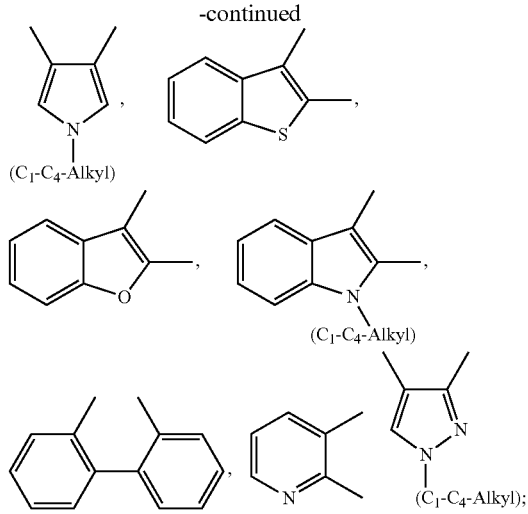

secondary phosphine $Z_1$ is the —$PR_2R_3$ group in which $R_2$ and $R_3$ are each independently a hydrocarbon radical or an O-atom(s) containing heterohydrocarbon radical which has 1 to 18 carbon atoms and is unsubstituted or substituted by $C_1$-$C_6$-alkyl, trifluoromethyl, $C_1$-$C_6$-alkoxy, trifluoromethoxy, $(C_1$-$C_4$-alkyl$)_2$amino, $(C_6H_5)_3$Si, $(C_1$-$C_{12}$-alkyl$)_3$Si, halogen, and the —$PR_2R_3$ group is bonded to the skeleton directly or via —$CH_2$—, —$(CH_2)$— or $C_2$-$C_6$-alkylidene; or $Z_1$ is the —P*(methyl)$R_1$ group;

$R_0$ is hydroxyl or methyl; and $R_1$ is one enantiomer of menthyl, bornyl or isopinocamphyl.

In this preferred embodiment, Q is more preferably radicals of the formulae

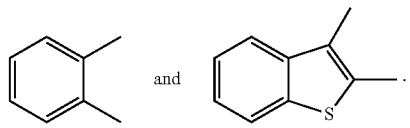

Another preferred subgroup of inventive compounds of the formula I is that of those in which Q when defined as 2,2'-biphenylene is an unsubstituted radical, or one substituted as detailed above, of the formula

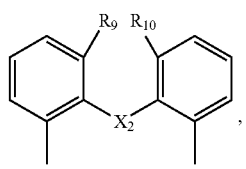

$X_2$ is a bond, —$CH_2$—, —$(CH_2)_2$—, $C_2$-$C_8$-alkylidene, cyclopentylidene, cyclohexylidene, —CH(O—$C_1$-$C_4$-alkyl), —O—, —S—, —$NR_{07}$— or —Si$(R_{07})_2$—;

$R_{07}$ is $C_1$-$C_4$-alkyl;

$R_9$ and $R_{10}$ are each a hydrogen atom, or $R_9$ and $R_{10}$ together are a bond or are —$CH_2$—, —$(CH_2)_2$— or $C_2$-$C_8$-alkylidene;

secondary phosphine $Z_1$ is the —$PR_2R_3$ group in which $R_2$ and $R_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$Si, halogen, and the —PR$_2$R$_3$ group is linked to the skeleton directly or via —CH$_2$—, —(CH$_2$)— or C$_2$-C$_6$-alkylidene; or Z$_1$ is the —P*(methyl)R$_1$ group;

R$_0$ is hydroxyl or methyl; and

R$_1$ is one enantiomer of menthyl, bornyl or isopinocamphyl.

A further preferred subgroup of inventive compounds of the formula I is that of those in which Q is unsubstituted 1,1'-ferrocenylene of the formula

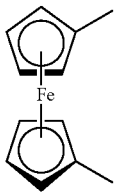

secondary phosphine Z$_1$ is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$Si, halogen, and the —PR$_2$R$_3$ group is linked to the skeleton directly or via —CH$_2$—, —(CH$_2$)— or C$_2$-C$_6$-alkylidene; or Z$_1$ is the —P*(methyl)R$_1$ group:

R$_0$ is hydroxyl or methyl; and

R$_1$ is one enantiomer of menthyl, bornyl or isopinocamphyl.

A further preferred subgroup of inventive compounds of the formula I is that of those in which Q is unsubstituted or C$_1$-C$_4$-alkyl- or phenyl-substituted C$_1$-C$_4$-alkylene, and particularly C$_1$- or C$_2$-alkylene;

secondary phosphine Z$_1$ is the —PR$_2$R$_3$ group in which R$_2$ and R$_3$ are each independently a hydrocarbon radical or an O-atom(s) containing heterohydrocarbon radical which has 1 to 18 carbon atoms and is unsubstituted or substituted by C$_1$-C$_6$-alkyl, trifluoromethyl, C$_1$-C$_6$-alkoxy, trifluoromethoxy, (C$_1$-C$_4$-alkyl)$_2$amino, (C$_6$H$_5$)$_3$Si, (C$_1$-C$_{12}$-alkyl)$_3$Si, halogen, and the —PR$_2$R$_3$ group is bonded to the skeleton directly or via —CH$_2$—, —(CH$_2$)— or C$_2$-C$_6$-alkylidene; or Z$_1$ is the —P*(methyl)R$_1$ group;

R$_0$ is hydroxyl or methyl; and

R$_1$ is one enantiomer of menthyl, bornyl or isopinocamphyl. In this preferred embodiment, Q is more preferably methylene.

The inventive compounds of the formula I are preparable by known or analogous processes for organometallic syntheses.

The inventive compounds of the formula I are obtainable in a simple manner, for example, from halogenated precursors, by first metallating the precursor, for example with lithium alkyl, then reacting the metallated compound with a dihalophosphine, a halomonoalkoxyphosphine or a halomono(dialkylamino)phosphine, and, in a last stage, forming the —*P(=O)HR$_1$ group by hydrolysis, or using organometallic reagents to introduce the methyl group. These reactions proceed with good yields and reaction products from the intermediate stages and the final stage can—if required—be purified by simple means, for example recrystallization and chromatographic purifications with achiral columns, for example on silica gels as the solid phase. In the recrystallization, it may be appropriate to convert the compounds of the formula I to phosphonium salts, for example with Cl$^-$, —Br$^-$, I$^-$, ClO$_4^-$, CF$_3$SO$_3^-$, CH$_3$SO$_3^-$, HSO$_4^-$, (CF$_3$SO$_2$)$_2$N$^-$, (CF$_3$SO$_2$)$_3$C$^-$ anions, tetraarylborates, for example B(phenyl)$_4^-$, B[bis(3,5-trifluoromethyl)phenyl]$_4^-$, B[bis(3,5-dimethyl)phenyl]$_4^-$, B(C$_6$F$_5$)$_4^-$ and B(4-methylphenyl)$_4^-$, BF$_4^-$, PF$_6^-$, SbCl$_6^-$, AsF$_6^-$ or SbF$_6$. Diastereomers of intermediates and end products can also be obtained by chromatography on chiral columns or recrystallization, if appropriate from salts of achiral or chiral acids, for example phenyllactic acid or α-amino acids (see for example J. Drabowicz et al. in Tetrahedron: Asymmetry 10 (1999) 2757-63). Alternatively, it is also possible to purify compounds of formula (I) by formation and purification, e.g. by fractional crystallization, of metal complexes.

Alternatively, compounds of the formula I where R$_0$ is methyl can also be obtained by reacting halogenated precursors (such as compounds of the formula II) with lithium-PR$_0$R$_1$ where R$_0$ is methyl.

Compounds of the formula I where Q is methylene can also be obtained by the processes described in the literature; see J. Wolf et al. in J. Chem. Soc., Dalton Trans. (1999) 1867 to 1875, or I. D. Gridnev et al. in Adv. Synth. Catal 343(1) (2001) 118-136.

Interesting compounds according to the invention are both enantiomers of the compounds selected from the group consisting of

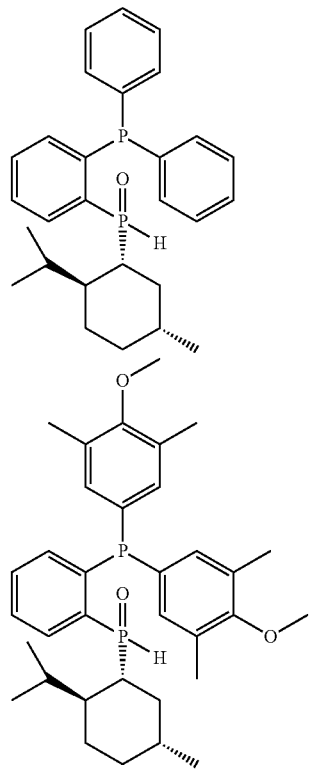

15
-continued
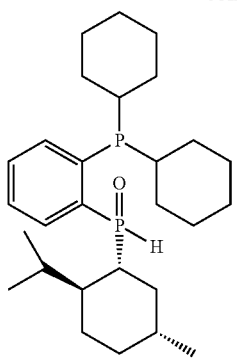
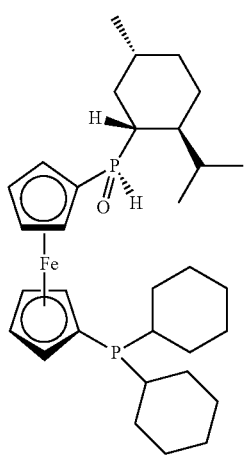
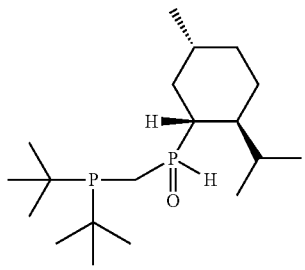
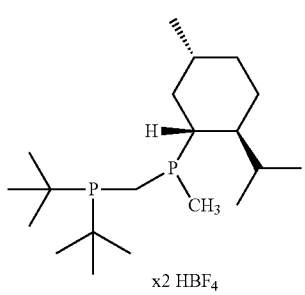
x2 HBF₄
16
-continued
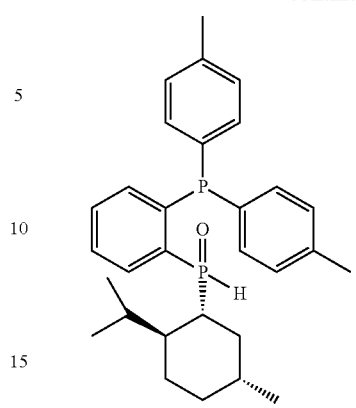
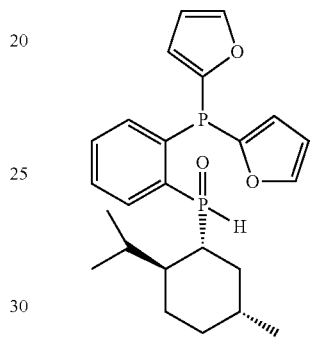
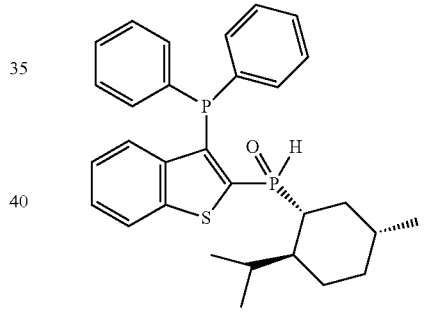
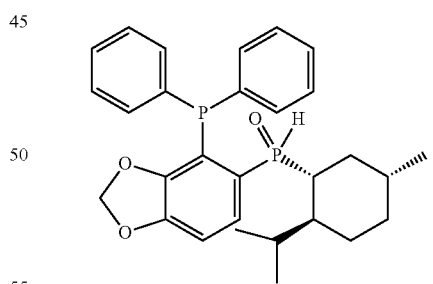
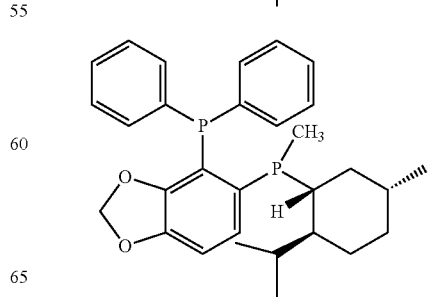

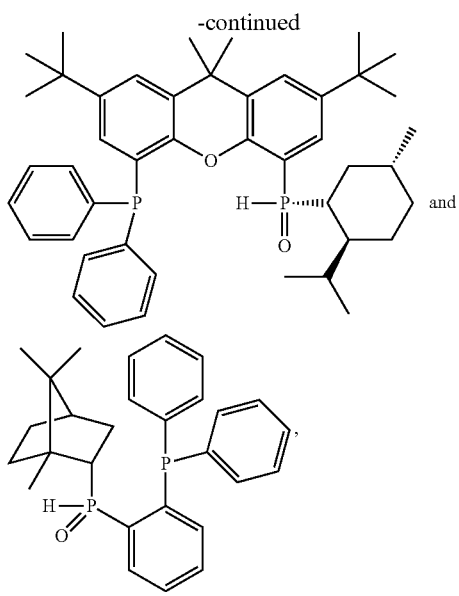

wherein the absolute configuration on the stereogenic phosphorus is R or S.

The invention further provides a process for preparing compounds of the formula I, characterized in that a compound of the formula II secondary phosphine-Q-Hal     (II)

in which secondary phosphine and Q are each as defined above and Hal is Cl, Br or I or active hydrogen is reacted with a metallating reagent and then with a halophosphine of the formula IIIa or of the formula IIIb $Hal_1\text{-}PX_3R_1$     (IIIa)

$(Hal_1)_2PR_1$     (IIIb)

in which $R_1$ is as defined above in formula I, including the preferences, $Hal_1$ is Cl, Br or I, and $X_3$ is $C_1$-$C_4$-alkoxy, $C_5$-$C_7$-cycloalkoxy or $(C_1$-$C_4$-alkyl$)_2$amino, and the compound of the formula IVa or of the formula IVb formed secondary phosphine-Q-P(Hal$_1$)R$_1$     (IVa)

secondary phosphine-Q-P(X$_3$)R$_1$     (IVb)

are hydrolysed to a compound of the formula I by methods such as, mixing the reaction mixture with water, or mixing the reaction mixture with water containing an acid, or mixing the reaction mixture with water containing a base, whereby the compounds of formula (IVa) or (IVb) can be added to the hydrolyzing medium or the hydrolyzing medium to the compounds of formula (IVa) or (IVb), the methyl group is introduced with a methylorganic compound, or a compound of formula (IVa) is reacted with a primary or secondary amine or an alcohol, optionally in presence of a base such as triethylamine, to form an aminophosphine or a phosphinite, which is then hydrolyzed by one of the methods described above or by reaction with a neat carboxylic acid such as formic acid or acetic acid.

Suitable acids for the hydrolysis of compounds of formula (IVa) and (IVb) are hydrochloric acid, sulphuric acid, formic acid, acetic acid, trifluoroacetic acid, methylsulfonic acid and benzenecarboxylic acid.

Suitable bases for the hydrolysis of compounds of formula (IVa) and (IVb) are NaOH, KOH, LiOH, $Na_2CO_3$, $K_2CO_3$ or tertiary amines such as triethylamine, di-isoproypylethylamine, N,N-dimethylaniline and pyridine.

The concentration of the acid or of the base is suitably 0.01-5 molar. The hydrolysis is suitably carried out at a temperature in a range 0° C. to 90° C., preferably 0-25° C.

The hydrolysis conditions influence the stereochemistry of the SPO group in compounds of formula (I). The ratio of the epimers formed may strongly depend on the pH of the hydrolysis medium.

Suitable primary or secondary amines or alcohols are compounds of the formula $H_2NR_{Xa}$ or $HN(R_{Xa})_2$ or $HOR_{Xa}$, whereby in $HN(R_{Xa})_2$ the two $R_{Xa}$ are the same or different, and where $R_{Xa}$ is a hydrocarbon.

$R_{Xa}$ may, for example, be $C_1$-$C_{12}$-alkyl, preferably $C_1$-$C_8$-alkyl and more preferably $C_1$-$C_4$-alkyl. Examples are methyl, ethyl, n- or i-propyl, n-, i- or t-butyl, pentyl, hexyl, octyl, decyl, undecyl and dodecyl.

$R_{Xa}$ may also, for example, be $C_5$-$C_8$-cycloalkyl, preferably $C_5$-$C_6$-cycloalkyl.

Examples are cyclopentyl, cyclohexyl and cyclooctyl.

$R_{Xa}$ may also, for example, be $C_5$-$C_8$-cycloalkylalkyl, preferably $C_5$-$C_6$-cycloalkylalkyl having, for example, 1 to 4 carbon atoms in the alkyl. Examples are cyclopentylmethyl, cyclohexylmethyl or -ethyl and cyclooctylmethyl.

$R_{Xa}$ may also, for example, be $C_6$-$C_{18}$-aryl and preferably $C_6$-$C_{10}$-aryl. Examples are phenyl or naphthyl.

$R_{Xa}$ may also, for example, be $C_7$-$C_{12}$-aralkyl, for example benzyl or 1-phenyleth-2-yl.

Compounds of the formula II are known or can be prepared by known or analogous processes.

The process conditions are known for organometallic syntheses and are not described in detail here. Details can be taken from the examples.

The inventive compounds of the formula I are ligands for metal complexes selected from the group of the transition metals, which are outstanding catalysts or catalyst precursors for asymmetric syntheses, for example the asymmetric hydrogenation of prochiral, unsaturated, organic compounds. When prochiral, unsaturated, organic compounds are used, a very high excess of optical isomers can be induced in the synthesis of organic compounds and a high chemical conversion can be achieved within short reaction times. The achievable enantioselectivities and catalyst activities are excellent. In addition, such ligands can also be used in other asymmetric addition or cyclization reactions.

The invention further provides metal complexes of transition metals of the transition groups of the Periodic Table of the Elements with a compound of the formulae I as ligands, where the equivalents ratio of ligand to metal is preferably about 2.2:1 to 0.9:1 and more preferably 1.1:1 to 0.9:1. Especially preferably, the equivalents ratio is around 1.1:1 to 1:1.

Among the transition metals, particular preference is given to metals selected from the group of Fe, Co, Ni, Cu, Ag, Au, Ru, Rh, Pd, Os, Ir. Very particularly preferred metals are Cu, Pd, Ru, Rh, Ir and Pt. Examples of organic syntheses are, as well as asymmetric hydrogenations of prochiral, unsaturated, organic compounds, amine couplings, enantioselective ring openings and hydrosilylations.

Particularly preferred metals are ruthenium, rhodium and iridium.

According to the oxidation number and coordination number of the metal atom, the metal complexes may contain further ligands and/or anions. They may also be cationic metal complexes. Such analogous metal complexes and their preparation have been described many times in the literature.

The metal complexes may, for example, correspond to the general formulae V and VI $$A_1 MeL_n \qquad (V)$$

$$(A_1 MeL_n)^{(z+)}(E^-)_z \qquad (VI)$$

in which $A_1$ is a compound of the formula I,

L represents identical or different monodentate, anionic or nonionic ligands, or two L represent identical or different bidentate, anionic or nonionic ligands;

n is 2, 3 or 4 when L is a monodentate ligand, or n is 1 or 2 when L is a bidentate ligand;

z is 1, 2 or 3;

Me is a metal selected from the group of Rh, Ir and Ru; where the metal has the oxidation states of 0, 1, 2, 3 or 4;

$E^-$ is the anion of an oxygen acid or complex acid; and the anionic ligands balance the charge of the 1, 2, 3 or 4 oxidation states of the metal.

For the compounds of the formulae I, the preferences and embodiments described above apply.

Monodentate nonionic ligands may, for example, be selected from the group of the olefins (for example ethylene, propylene), allyls (allyl, 2-methallyl), solvating solvents (nitriles, linear or cyclic ethers, optionally N-alkylated amides and lactams, amines, phosphines, alcohols, carboxylic esters, sulphonic esters), nitrogen monoxide and carbon monoxide.

Monodentate anionic ligands may, for example, be selected from the group of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands may, for example, be selected from the group of the linear and cyclic diolefins (for example hexadiene, cyclooctadiene, norbornadiene), dinitriles (malonitrile), optionally N-alkylated dicarboxamides, diamines, diphosphines, diols, acetonylacetonates, dicarboxylic diesters and disulphonic diesters.

Bidentate anionic ligands may, for example, be selected from the group of the anions of dicarboxylic acids, disulphonic acids and diphosphonic acids (for example from oxalic acid, malonic acid, succinic acid, maleic acid, methylenedisulphonic acid and methylenediphosphonic acid).

Preferred metal complexes are also those in which $E^-$ represents anions of oxygen acids selected from the group of $ClO_4^-$, $CF_3SO_3^-$, $CH_3SO_3^-$, $HSO_4^-$, and anions of complex acids selected from the group of tetraarylborates, for example $B(phenyl)_4^-$, $B[bis(3,5-trifluoromethyl)phenyl]_4^-$, $B[bis(3,5-dimethyl)phenyl]_4^-$, $B(C_6F_5)_4^-$ and $B(4-methylphenyl)_4^-$, and $BF_4^-$, $PF_6^-$, $SbCl_6^-$, $AsF_6^-$ or $SbF_6^-$. Other suitable anions $E^-$ are —$Cl^-$, —$Br^-$, —$I^-$, $(CF_3SO_2)_2N^-$ and $(CF_3SO_2)_3C^-$.

Especially preferred metal complexes which are particularly suitable for hydrogenations correspond to the formulae VII and VIII $$[A_1 Me_2 YZ] \qquad (VII)$$

$$[A_1 Me_2 Y]^+ E_1^- \qquad (VIII)$$

in which
$A_1$ is a compound of the formula I;
$Me_2$ is rhodium or iridium;

Y represents two olefins or one diene;

Z is Cl, Br or I; and $E_1^-$ is the anion of an oxygen acid or complex acid.

For the compounds of the formulae I, the preferences and embodiments described above apply.

When Y is defined as olefin, it may be $C_2$-$C_{12}$-, preferably $C_2$-$C_6$- and more preferably $C_2$-$C_4$-olefins. Examples are propene, but-1-ene and particularly ethylene. The diene may contain 5 to 12 and preferably 5 to 8 carbon atoms, and the dienes may be open-chain, cyclic or polycyclic dienes. The two olefin groups of the diene are preferably connected by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene or 1,5-hexadiene, 1,5-cyclooctadiene or norbornadiene.

In formula VIII, Z is preferably Cl or Br. Examples of $E_1^-$ are $BF_4^-$, $ClO_4^-$, $CF_3SO_3^-$, $CH_3SO_3^-$, $HSO_4^-$, $B(phenyl)_4^-$, $B[bis(3,5-trifluoromethyl)phenyl]_4^-$, $PF_6^-$, $SbCl_6^-$, $AsF_6^-$ or $SbF_6^-$.

The inventive metal complexes are prepared by methods known in the literature (see also U.S. Pat. No. 5,371,256, U.S. Pat. No. 5,446,844, U.S. Pat. No. 5,583,241, and E. Jacobsen, A. Pfaltz, H. Yamamoto (Eds.), Comprehensive Asymmetric Catalysis I to III, Springer Verlag, Berlin, 1999, and literature cited therein).

The inventive metal complexes are homogeneous catalysts or catalyst precursors activable under the reaction conditions, which can be used for asymmetric addition reactions onto prochiral, unsaturated, organic compounds; see E. Jacobsen, A. Pfaltz, H. Yamamoto (Eds.), Comprehensive Asymmetric Catalysis I to III, Springer Verlag, Berlin, 1999, and B. Cornils et al., in Applied Homogeneous Catalysis with Organometallic Compounds, Volume 1, Second Edition, Wiley VCH-Verlag (2002). Further applications are, for example, the amination of aromatics or heteroaromatics which contain leaving groups, for example halide or sulphonate, with primary or secondary amines using palladium complexes, or the preferably Rh-catalysed enantioselective ring-opening reaction of oxabicyclic alkanes (M. Lautens et al. in Acc. Chem. Res. Volume 36 (203), pages 48-58.

The metal complexes can, for example, be used for asymmetric hydrogenation (addition of hydrogen) of prochiral compounds with carbon/carbon or carbon/heteroatom double bonds. Such hydrogenations with soluble homogeneous metal complexes are described, for example, in Pure and Appl. Chem., Vol. 68, No. 1, pp. 131-138 (1996). Preferred unsaturated compounds for hydrogenation contain C=C (prochiral alkenes), C=N (prochiral ketimines), C=N—N (prochiral ketohydrazones), C=N—O (prochiral ketoximes) and/or C=O (prochiral ketones) groups. For the hydrogenation, according to the invention, preference is given to using metal complexes of ruthenium, rhodium and iridium.

The invention further provides for the use of the inventive metal complexes as homogeneous catalysts for preparing chiral organic compounds by asymmetric addition of hydrogen onto a carbon- or carbon-heteroatom double bond in prochiral organic compounds.

A further aspect of the invention is a process for preparing chiral organic compounds by asymmetric addition of hydrogen onto a carbon or carbon-heteroatom double bond in prochiral organic compounds in the presence of a catalyst, characterized in that the addition is carried out in the presence of catalytic amounts of at least one inventive metal complex.

Preferred prochiral, unsaturated compounds for hydrogenation may contain one or more, identical or different C=C, C=N and/or C=O groups, in open-chain or cyclic organic compounds, where the C=C, C=N and/or C=O groups may be part of a ring system or are exocyclic groups. The prochiral unsaturated compounds may be alkenes, cycloalkenes, heterocycloalkenes, and open-chain or cyclic ketones, α,β-diketones, α- or β-ketocarboxylic acids, and the α,β-keto acetals or ketals thereof, esters and amides, ketimines, ketoximes and kethydrazones. Alkenes, cycloalkenes, heterocycloalkenes also include enamides.

The process according to the invention can be carried out at low or elevated temperatures, for example temperatures of −20 to 150° C., preferably of −10 to 100° C., and more preferably of 10 to 80° C. The optical yields are generally better at lower temperature than at higher temperatures.

The process according to the invention can be carried out at standard pressure or elevated pressure. The pressure may, for example, be $10^5$ to $2\times10^7$ Pa (pascals). Hydrogenations can be carried out at standard pressure or elevated pressure.

Catalysts are preferably used in amounts of 0.00001 to 10 mol %, more preferably 0.00001 to 5 mol %, and especially preferably 0.00001 to 2 mol %, based on the compound to be hydrogenated.

The preparation of the ligands and catalysts and the hydrogenation can be carried out without or in the presence of an inert solvent, it being possible to use one solvent or mixtures of solvents. Suitable solvents are, for example, aliphatic, cycloaliphatic and aromatic hydrocarbons (pentane, hexane, petroleum ether, cyclohexane, methylcyclohexane, benzene, toluene, xylene), aliphatic halohydrocarbons (methylene chloride, chloroform, di- and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylacetamide, dimethylformamide), acyclic ureas (dimethylimidazoline), and sulphoxides and sulphones (dimethyl sulphoxide, dimethyl sulphone, tetramethylene sulphoxide, tetramethylene sulphone) and optionally fluorinated alcohols (methanol, ethanol, propanol, butanol, ethylene glycol monomethyl ether, ethylene glycol monoethyl ether, diethylene glycol monomethyl ether, 1,1,1-trifluoroethanol) and water. Suitable solvents are also low molecular weight carboxylic acids, for example acetic acid.

The reactions can be carried out in the presence of cocatalysts, for example quaternary ammonium halides (tetrabutylammonium chloride, bromide or iodide) or protic acids, for example mineral acids such as HCl or strong organic acids such as trifluoroacetic acid, or mixtures of such halides and acids (see for example U.S. Pat. No. 5,371,256, U.S. Pat. No. 5,446,844 and U.S. Pat. No. 5,583,241 and EP-A-0 691 949). The presence of fluorinated alcohols, for example 1,1,1-trifluoroethanol, can also promote the catalytic reaction. The addition of bases, for example tertiary amines or phosphines, alkali metal hydroxides, secondary amides, alkoxides, carbonates and hydrogencarbonates may also be advantageous. The selection of a cocatalyst may be guided principally by the metal in the metal complex and the substrate. In the hydrogenation of prochiral aryl ketimines, the use of iridium complexes in combination with tetra-$C_1$-$C_4$-alkylammonium iodides and mineral acids, preferably HI, has been found to be useful.

The metal complexes used as catalysts can be added as separately prepared isolated compounds, or else be formed in situ before the reaction and then mixed with the substrate to be hydrogenated. It may be advantageous to additionally add ligands in the case of reaction using isolated metal complexes, or to use an excess of the ligands in the case of in situ preparation. The excess may, for example, be 1 to 6 and preferably 1 to 2 mol, based on the metal compound used for the preparation.

The process according to the invention is generally carried out by initially charging the catalyst and then adding the substrate, optionally reaction assistants and the compound to be added on, and then starting the reaction. Gaseous compounds to be added on, for example hydrogen, are preferably injected. The process can be carried out in various reactor types, continuously or batchwise.

The chiral organic compounds preparable in accordance with the invention are active substances or intermediates for preparing such substances, especially in the sector of production of aromas and odorants, pharmaceuticals and agrochemicals.

The examples which follow illustrate the invention. All reactions are carried out under argon with exclusion of air and with degassed solvents. The yields are not optimized. Abbreviations: THF=tetrahydrofuran; TBME=tert-butyl methyl ether; nbd=norbornadiene; cod=cycloocta-1,5-diene; acac=acetylacetonate.

For clarification the absolute configurations of the stereogenic phosphorus was not determined and is not known. Therefore, in the drawings of the structures, the configuration of the stereogenic phosphorous is not represented.

A) PREPARATION OF INTERMEDIATES

The compound o-bromophenyldiphenylphosphine is commercially available. The compound o-bromophenyldicyclohexylphosphine is prepared as described by M. Murata et al., Tetrahedron, 60 (2004) 7397-7403.

(L)-menthyldichlorophosphine is prepared as described in the literature: M. Minato, T. Kaneko, S. Masauji, T. Ito, J. Organometal. Chem., 691 (2006) 2483-8 (and literature cited therein); A. Hinke, W. Kuchen, Phosphorous and Sulphur, 15 (1983) 93-98.

The synthesis of 3-diphenylphosphine-benzothiophene is described in M. Kesselgruber et al., patent WO 2006111535, the synthesis of o-bromophenyl-di-para-tolylphosphine in J. F. Hartwig et al., J. Amer. Chem. Soc, 129 (2007) 7734 and the preparation of 4-bromo-5-diphenylphosphino-2,7-di-tert-butyl-9,9-dimethylxanthene in W. N. M. van Leeuwen et al., Chem. Commun. (2000) 333.

1R-2S-4R-2-Bromo-1,7,7-trimethyl-bicyclo[2.2.1]heptane is prepared from (−)-α-pinene according to H. G. Kuivila et al., J. Org. Chem., 51 (1986), 4947-4953.

Example A1

Preparation of o-bromophenylbis(3,5-dimethyl-4-methoxyphenyl)-phosphine A1

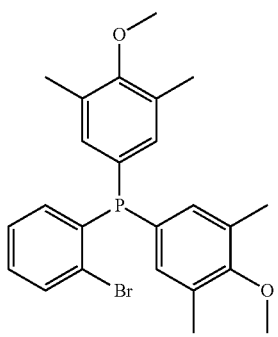

A1

To a solution of 9.67 g (34.2 mmol) of 1-bromo-2-iodobenzene in 30 ml of THF are added dropwise, at −78° C., 17.6 ml (37.6 mmol) of an isopropylmagnesium chloride solution (2 molar in THF). The mixture is stirred at a temperature between −30° C. and −40° C. for a further 1 hour, then cooled again to −78° C., and a solution of 12.66 g (37.6 mmol) of bis(3,5-dimethyl-4-methoxyphenyl)chlorophosphine in 10 ml of THF and 10 ml of TBME is added. The cooling is removed and the reaction mixture is stirred at room temperature overnight. The resulting solution is admixed with 50 ml of water and extracted with water/TBME. The organic phases are collected and dried over sodium sulphate, and the solvent is distilled off under reduced pressure on a rotary evaporator. The crude product is purified by chromatography (silica gel 60; eluent=1:1 heptane/ethyl acetate). The desired product is obtained in the form of white crystals in a yield of 76%.

$^{31}$P NMR ($C_6D_6$, 121 MHz): δ −5.2 (s); $^1$H NMR ($C_6D_6$, 300 MHz), characteristic signals: δ 7.44-6.6 (various m, 8H), 3.28 (s, 6H), 2.06 (s, 12H).

Example A2

Preparation of 1-dicyclohexylphosphino-1'-bromoferrocene A2

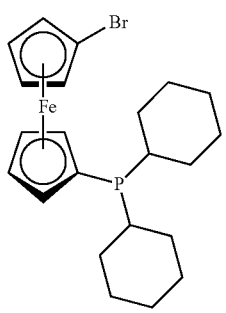

A2

To a solution of 103 g (0.3 mol) of 1,1'-dibromoferrocene in 300 ml of THF are added dropwise, at a temperature of <−30° C., 120 ml (0.3 mol) of n-BuLi (2.5 M in hexane).

The mixture is stirred at this temperature for a further 1.5 hour. The mixture is then cooled to −50° C., and 66.2 ml (0.3 mol) of dicyclohexylphosphine chloride are added dropwise sufficiently slowly that the temperature does not rise above −45° C. After stirring for a further 10 minutes, the temperature is allowed to rise to room temperature and the mixture is stirred for another hour. After 150 ml of water have been added, the reaction mixture is extracted by shaking with hexane. The organic phases are dried over sodium sulphate and the solvent is distilled off under reduced pressure on a rotary evaporator. The residue is crystallized in ethanol. The product A2 is obtained with a yield of 84% (yellow solid).

$^{31}$P NMR (121.5 MHz, C6D6): δ −8.3 (s); $^1$H NMR (300 MHz, C6D6): δ 4.41 (m, 2H), 4.26 (m, 2H), 4.23 (m, 2H), 3.97 (m, 2H), 1.20-2.11 (m, 22H).

Example A3

Preparation of the borane adduct of di-t-butylmethylphosphine A3

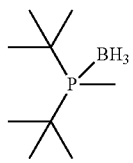

A3

To a solution of 15.54 g of (t-butyl)$_2$PCl (86.00 mmol) in 120 ml of THF are added dropwise, at −78° C. within 60 minutes, 59.13 ml of MeLi (94.60 mmol, 1.6 M in hexane). The resulting suspension is stirred at −78° C. for 1 hour, then the cooling bath is removed and the mixture is stirred at room temperature for 1 hour. Then, within 20 minutes, 9.78 ml of BH$_3$—SMe$_2$ (103.20 mmol) are added dropwise and the suspension is stirred at room temperature for 2 hours. Subsequently, 60 ml of saturated NaHCO$_3$ solution (60 ml) are added slowly to the mixture, which is extracted with TBME. The combined organic phases are dried over Na$_2$SO$_4$ and the solvent is distilled off on a rotary evaporator. The resulting oil is purified by column chromatography (silica gel 60; eluent=3:1 heptane/TBME). The product A3 is obtained in the form of colourless crystals in a yield of 80%.

Example A4

Preparation of o-bromophenylbis(2-furyl)-phosphine A4

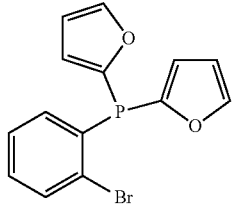

A4

Compound A4 is prepared in analogy to compound A1, with the exception that bis-(2-furyl)chlorophosphine is added instead of bis(3,5-dimethyl-4-methoxyphenyl)chlorophosphine. The white solid product is obtained after crystallization in heptane in a yield of 65%. $^{31}$P NMR ($C_6D_6$, 121 MHz):

δ −49.3 (s); $^1$H NMR (C$_6$D$_6$, 300 MHz), characteristic signals: δ 7.3-7.2 (m, 2H), 7.18 (m, 2H), 6.82 (t, 1H), 6.70-6.56 (m, 3H), 6.0 (m, 2H).

Example A5

Preparation of 4-bromo-3-diphenylphosphino-1,2-methylene dioxy)benzene A5

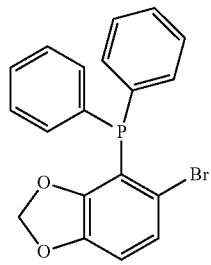

A5

To a solution of 55 mmol lithiumdiisopropylamide (freshly prepared from 55 mmol diisopropylamine and 55 mmol n-BuLi (1.6M in hexane) in 115 ml THF) are added dropwise, at −78° C. within 10 minutes, 6.02 ml (50 mmol) 4-bromo-1,2-(methylenedioxy)benzene. After stirring for 1 hour at approx. −70° C., 10.16 ml (55 mmol) chlorodiphenylphosphine are added dropwise within 30 minutes. After stirring for 1 hour at the same temperature, the temperature is allowed to rise to room temperature. After addition of 25 ml water and 100 ml ethylacetate, HCl 2N is added until the water phase is slightly acidic. The organic phase is separated, washed with Na$_2$CO$_3$, dried over Na$_2$SO$_4$ and the solvent is distilled off on a rotary evaporator. The raw product is suspended and stirred in boiling TBME and, after cooling to room temperature filtered and washed with heptane. The obtained solid product is almost white and sufficiently pure for further use. If required, it can be further purified by column chromatography (silica gel 60; eluent=5:1 heptane/toluene). The product A5 is obtained in the form of colourless crystals in a yield of 70%.

$^{31}$P NMR (C$_6$D$_6$, 121 MHz): δ −5.12 (s); $^1$H NMR (C$_6$D$_6$, 300 MHz), characteristic signals: δ 7.51 (m, 4H), 7.07 (m, 6H), 6.92 (d of d, 1H), 6.25 (d, 1H), 4.83 (s, 2H).

Example A6

Preparation of Dichloro(1R-2S-4R-1,7,7-trimethyl-bicyclo[2.2.1]heptan-2-yl) phosphine A6

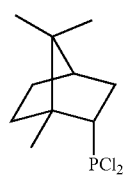

A6

565 mg Mg turnings (23.5 mmol) are suspended in THF (20 mL) and activated with a small amount of iodine. The mixture is heated to reflux and a solution of 1R-2S-4R-2-bromo-1,7,7-trimethyl-bicyclo[2.2.1]heptane (4.80 g, 22.1 mmol) in THF (10 mL) is added. After 1 hour the solution is allowed to cool to room temperature and transferred via cannula to a solution of bis(diethylamino)chlorophosphine (4.75 mL, 22.5 mmol) in THF (10 mL) at −78° C. The resulting solution is stirred for another 10 min at −78° C., warmed up to room temperature and concentrated to half volume. The solution is cooled in an ice bath and 46 ml (92 mmol) HCl (2 M in Et2O) are added. After warming up to room temperature the solution is diluted with pentane (10 mL), filtered and the solvent removed under reduced pressure. The crude product is distilled bulb to bulb to give the desired compound A6 (2.84 g, yield 54%) as a colorless liquid.

$^{31}$P-NMR (CD$_2$Cl$_2$, 121 MHz): δ=195.7 (s).

$^1$H-NMR (CD$_2$Cl$_2$): δ 0.89 (s, 3H), 0.94 (s, 3H), 1.07 (s, 3H), 1.18-1.30 (m, 1H), 1.25-1.39 (m, 1H), 1.50-1.64 (m, 1H), 1.72-1.80 (m, 1H), 1.75-1.79 (m, 1H), 1.76-1.88 (m, 1H), 2.13-2.26 (m, 1H), 2.67 (m).

B) PREPARATION OF THE LIGANDS

Example B1

Preparation of the Secondary Phosphine Oxide Ligand B1

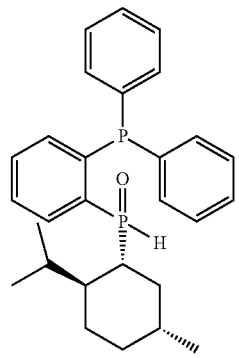

B1

To a solution of 2.19 g (6.42 mmol) of o-bromophenyl-diphenylphosphine in 7 ml of THF and 5 ml of TBME are added dropwise, at −78° C., 4.01 ml (6.42 mmol) of n-butyl-lithium (1.6 M in hexane). The resulting suspension is stirred at −78° C. for a further 1.5 hour. Then the suspension is injected using elevated argon pressure with the aid of a cannula into a reaction vessel, in which a solution of 1.55 g (6.42 mmol) of (L)-menthyldichlorophosphine in 5 ml of TBME is being stirred at −78° C. After addition, 3 ml of THF are used to rinse it in and the suspension is then stirred without cooling for a further 1.5 hour. Then 5 ml of water and 0.5 ml of 1N NaOH are added, and the reaction mixture is stirred until the phosphine chloride has been hydrolysed fully and finally extracted with TBME. The organic phases are collected and dried over sodium sulphate, and the solvent is distilled off under reduced pressure on a rotary evaporator. The crude yield is virtually quantitative. A $^{31}$P NMR of the white solid crude product shows that predominantly one of the two possible diastereomeric P-chiral ligands has formed (diastereomer ratio about 9:1). It is possible by chromatography (silica gel 60; eluent=1:1 heptane/ethyl acetate) to isolate the main stereoisomer in pure form, according to NMR analysis, as a white solid (yield 70%). $^{31}$P NMR of main diastereomer (C$_6$D$_6$, 121 MHz): δ 16.4 (d), −19.4 (d); $^1$H NMR of main diastereomer (C$_6$D$_6$, 300 MHz), characteristic signals: δ 8.64 (dd, J=471 Hz, J=5.1 Hz, 1H), 8.63-8.56 (m, 1H), 7.23-6.94 (various m, 13H), 2.77-0.3 (various m, 10H), 1.07 (d, 3H), 0.97 (d, 3H), 0.55 (d, 3H).

Example B1'

Preparation of the Secondary Phosphine Oxide Ligand B1 with the Inversed Configuration of the Phosphorous of the SPO Group

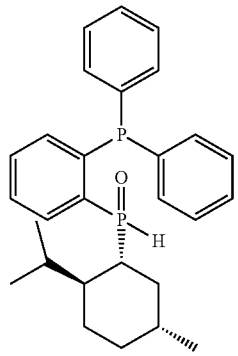

B1'

To a solution of 2.19 g (6.42 mmol) of o-bromophenyl-diphenylphosphine in 7 ml of THF and 5 ml of TBME are added dropwise, at −78° C., 4.01 ml (6.42 mmol) of n-butyllithium (1.6 M in hexane). The resulting suspension is stirred at −78° C. for a further 1.5 hour. Then the suspension is injected using elevated argon pressure with the aid of a cannula into a reaction vessel, in which a solution of 1.55 g (6.42 mmol) of (L)-menthyldichlorophosphine in 5 ml of TBME is being stirred at −78° C. After addition, 3 ml of THF are used to rinse it in and the suspension is then stirred without cooling for a further 1.5 hour. Then the solvent is distilled off under reduced pressure. 20 ml of toluene and 2 ml of benzylamine are added to the residue and the mixture is stirred overnight. This reaction mixture is then added to 20 ml of formic acid to give, according to $^{31}$P-NMR, an approx. 1:1 mixture of the product B1 and B1'. The mixture is extracted with toluene, the organic phases are collected, washed with water, dired over Na$_2$SO$_4$ and the solvents distilled off under reduced pressure. Pure product B1' is obtained as a colorless oil by column chromatography (silica gel 60; eluent=heptane/ethylacetate 2:1).

$^{31}$P NMR (C$_6$D$_6$, 121 MHz): δ 30.95 (d), −17.13 (d); $^1$H NMR (C$_6$D$_6$, 300 MHz), characteristic signals: δ 8.03 (dd, J=467 Hz, 1H), 8.55-8.38 (m, 1H), 7.4-6.7 (various m, 13H), 2.6-0.6 (various m, 10H), 0.95 (d, 3H), 0.80 (d, 3H), 0.35 (d, 3H).

Example B2

Preparation of the Secondary Phosphine Oxide Ligand B2

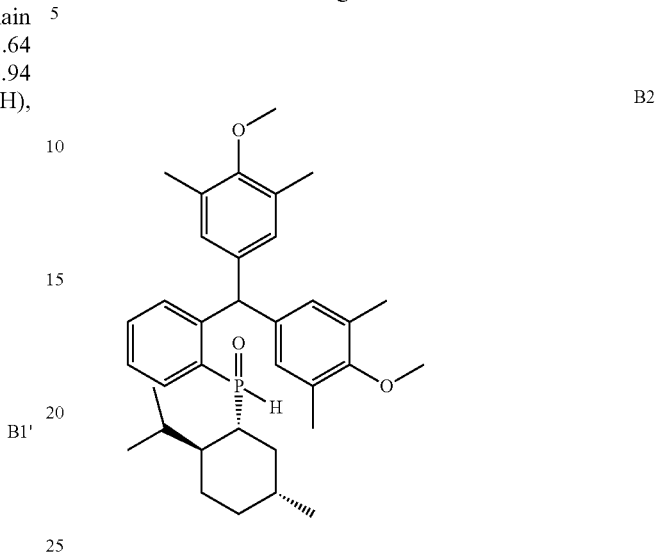

B2

Compound B2 is prepared analogously to compound B1 proceeding from compound A1 and (L)-menthyldichlorophosphine. The crude yield is almost quantitative. A $^{31}$P NMR of the white solid crude product shows that predominantly one of the two possible diastereomeric P-chiral ligands has formed (diastereomer ratio about 9:1). It is possible by chromatography (silica gel 60; eluent=1:1 heptane/ethyl acetate) to isolate the main stereoisomer in pure form, according to NMR analysis, as a white solid (yield 62%).

$^{31}$P NMR of main diastereomer (C$_6$D$_6$, 121 MHz): δ 16.1 (d), −21.2 (d): $^1$H NMR of main diastereomer (C$_6$D$_6$, 300 MHz), characteristic signals: δ 8.78 (dd, J=471 Hz, J=5.5 Hz, 1H), 8.65 (m, 1H), 7.44 (m, 1H), 7.15-7.02 (various m, 6H), 3.29 (d, 6H), 2.8-0.3 (various m, 10H), 2.05 (d, 3H), 1.12 (d, 3H), 0.99 (d, 3H), 0.57 (d, 3H).

Example B3

Preparation of the Secondary Phosphine Oxide Ligand B3

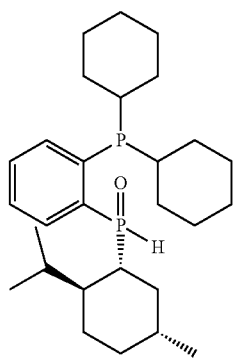

B3

To a solution of 1.05 g (2.97 mmol) of o-bromophenyldicyclohexylphosphine in 4 ml of TBME are added dropwise, at −78° C., 1.9 ml (2.97 mmol) of n-butyllithium (1.6 M in hexane). The resulting suspension is stirred at −78° C. for a further 1.5 hour. Then the suspension is diluted somewhat by adding 2 ml of TBME, and 0.75 g (2.97 mmol) of (L)-menthyldichlorophosphine are rapidly added dropwise. The cooling is removed and the mixture is stirred for a further 1 hour. Then 10 ml of water are added, and the reaction mixture is stirred overnight and finally extracted with TBME. The organic phases are collected and dried over sodium sulphate, and the solvent is distilled off under reduced pressure on a rotary evaporator. The crude yield is virtually quantitative. A $^{31}$P NMR of the white solid crude product shows that predominantly one of the two possible diastereomeric P-chiral ligands has formed (diastereomer ratio about 8:1). It is possible by chromatography (silica gel 60; eluent=1:1 heptane/ethyl acetate) to isolate the main stereoisomer in pure form, according to NMR analysis, as a white solid. Yield>35% (further product present in mixed fractions).

$^{31}$P NMR of main diastereomer (C$_6$D$_6$, 121 MHz): δ 18.4 (d), −16.4 (d); $^1$H NMR of main diastereomer (C$_6$D$_6$, 300 MHz), characteristic signals: δ 8.68 (dd, J=469 Hz, J=3.6 Hz, 1H), 8.60 (m, 1H), 7.32-7.07 (various m, 3H), 2.9-0.9 (various m, 32H), 1.18 (d, 3H), 1.04 (d, 3H), 0.68 (d, 3H).

Example B4

Preparation of the Two Diastereomers of the Secondary Phosphine Oxide Ligand B4

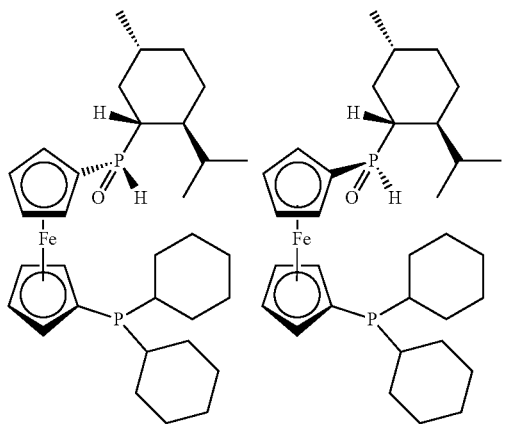

Diastereomers B4 and B4' (Absolute Configuration is not Known)

Compound B4 is prepared analogously to compound B1 proceeding from compound A2 and (L)-menthyldichlorophosphine. The crude yield is almost quantitative. A $^{31}$P NMR of the orange crude product shows that both possible diastereomeric P-chiral ligands have formed in about equal amounts (diastereomer ratio about 1:1). It is possible by simple chromatography (silica gel 60; eluent=2:1 heptane/ethyl acetate) to isolate both stereoisomers with a purity of about 95%: diastereomer B4, (first fraction in the chromatography): yield 32%, orange solid; diastereomer B4' (second fraction in the chromatography): yield 20%, orange, almost solid oil.

$^{31}$P NMR of diastereomer B4 (C$_6$D$_6$, 121 MHz): δ 30.73 (s), −7.91 (d); $^1$H NMR of diastereomer B4 (C$_6$D$_6$, 300 MHz), characteristic signals: δ 7.53 (d, J=456 Hz, 1H), 4.78 (m, 1H), 4.60 (m, 1H), 4.53-4.48 (m, 2H), 4.28 (m, 2H), 4.23 (m, 1H), 4.10 (m, 1H), 2.8-0.4 (various m, 32H), 0.95 (d, 3H), 0.93 (d, 3H), 0.73 (d, 3H).

$^{31}$P NMR of diastereomer B4' (C$_6$D$_6$, 121 MHz): δ 31.2 (s), −7.96 (d); $^1$H NMR of diastereomer B4' (C$_6$D$_6$, 300 MHz), characteristic signals: δ 7.51 (d, J=456 Hz, 1H), 4.79 (m, 1H), 4.67 (m, 1H), 4.55 (m, 2H), 4.25 (m, 3H), 4.15 (m, 1H), 2.6-0.6 (various m, 41H).

Example B5

Preparation of the Secondary Phosphine Oxide Ligand B5

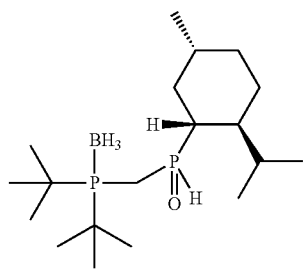

B5-BH$_3$

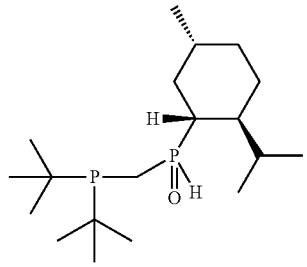

B5

To a solution of 2 g (11.5 mmol) of compound A3 in 16 ml of THF are added dropwise, at −25° C. within 60 minutes, 8.9 ml (11.5 mmol) of s-BuLi (1.3 M). The cooling is removed and the mixture is stirred at room temperature for a further 1 hour. This solution is then injected using elevated argon pressure with the aid of a cannula into a reaction vessel, in which a solution of 2.77 g (11.5 mmol) of L-menthyldichlorophosphine in 12 ml of TBME is being stirred at −78° C. After addition, stirring is continued at −78° C. for another 1 hour and then without cooling at room temperature for 1.5 hour. Then 10 ml of water are added, and the reaction mixture is stirred overnight and finally extracted with TBME. The organic phases are collected and dried over sodium sulphate, and the solvent is distilled off under reduced pressure on a rotary evaporator. The crude yield is virtually quantitative. A $^{31}$P NMR of the colourless, almost solid crude product shows that predominantly one of the two possible diastereomeric P-chiral ligands has formed (diastereomer ratio about 3:1). The crude product is stirred in heptane, which forms a fine white suspension in which the main diastereomer is enriched. This suspension is washed repeatedly with heptane. After recrystallization in heptane with 0.5% ethanol, the main diastereomer of compound B5-BH$_3$ is obtained with high optical purity, according to NMR analysis, in the form of white crystals.

$^{31}$P NMR of main diastereomer (C$_6$D$_6$, 121 MHz): δ 47.7 (broad m), 30.43 (d);

$^1$H NMR of main diastereomer (C$_6$D$_6$, 300 MHz), characteristic signals: δ 7.57 (d, J=482 Hz, 1H), 8.60 (m, 1H), 2.5-0.6 (various m, 10H), 1.25 (d, 9H), 1.01 (d, 9H), 0.93 (d, 3H), 0.8-0.72 (m, 6H).

Release of ligand B5: 80 mg of the borane adduct B5-BH₃ are kept at reflux in 5 ml of diethylamine over 30 minutes, and the diethylamine is subsequently distilled off under reduced pressure. This operation is repeated twice. The air-sensitive, colourless ligand B5 is obtained as a colourless, thick oil, which crystallizes at approx. 4° C. According to NMR, the ligand released is not entirely pure.

$^{31}$P NMR of main diastereomer (C$_6$D$_6$, 121 MHz): δ 41.2 (d), 21.4 (d); $^1$H NMR of main diastereomer (C$_6$D$_6$, 300 MHz), characteristic signals: δ 7.14 (d of broad multiplets, J=456 Hz, 1H).

Example B6

Preparation of the P-Chiral Phosphine B6

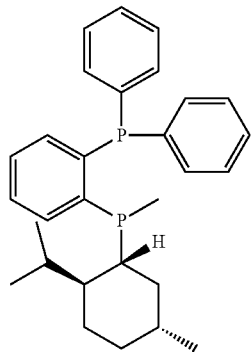

B6

To a solution of 0.92 g (2.7 mmol) of o-bromodiphenylphosphine in 2 ml of THF and 4 ml of TBME are added dropwise, at −78° C., 1.69 ml (2.7 mmol) of n-butyllithium (1.6 M in hexane). The resulting suspension is stirred at −78° C. for a further 1.5 hour. Then the suspension is injected using elevated argon pressure with the aid of a cannula into a reaction vessel, in which a solution of 0.65 g (2.7 mmol) of (L)-menthyldichlorophosphine in 2 ml of TBME is being stirred at −78° C. It is rinsed with 4 ml of THF and the suspension is then stirred without cooling for a further 2 hours.

Then 1.13 ml (3.2 mmol) of methylmagnesium chloride (3M in THF) are added and the reaction mixture is stirred overnight. Subsequently, it is extracted with water and TBME. The organic phases are collected and dried over sodium sulphate, and the solvent is distilled off under reduced pressure on a rotary evaporator. A $^{31}$P NMR of the almost solid crude product shows that predominantly one of the two possible diastereomeric P-chiral ligands has formed (diastereomer ratio about 9:1). The purification is effected by chromatography (silica gel 60; eluent=2:1 heptane/toluene) and subsequent recrystallization of the main fraction in methanol. The main diastereomer, which is optically pure according to NMR, is obtained as a white crystalline solid.

$^{31}$P NMR of main diastereomer (C$_6$D$_6$, 121 MHz): δ −14.7 (d), −35.5 (d); $^1$H NMR of main diastereomer (C$_6$D$_6$, 300 MHz), characteristic signals: δ 7.43-6.9 (various m, 14H), 2.73 (m, 1H), 2.11 (m, 1H), 1.62 (m, 2H), 1.15 (d, 3H), 1.05 (d, 3H), 0.94 (d, 3H), 0.68 (s, 3H).

Example B7

Preparation of the P-Chiral Phosphine B7 (HBF$_4$ Salt)

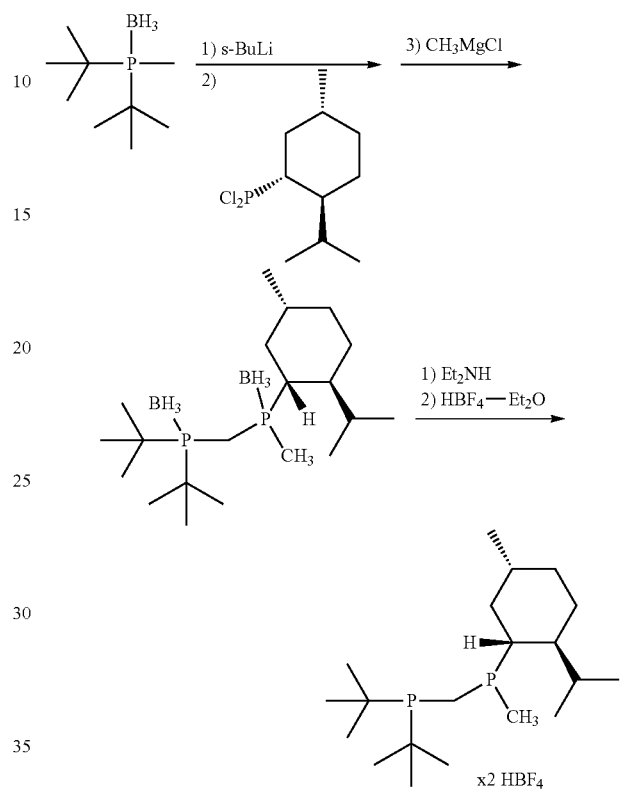

a) Preparation of the Diborane Adduct of B7

To a solution of 10 g (57.45 mmol) of the borane adduct of di-t-butylmethylphosphine in 80 ml of THF are added dropwise, at −25° C. within 60 min, 44.2 ml (57.45 mmol) of s-BuLi (1.3 M). The cooling is removed and the mixture is stirred at room temperature for a further 1 hour. This solution is then injected within 2 hours using elevated argon pressure with the aid of a cannula into a reaction vessel, in which a solution of 13.85 g (57.45 mmol) of L-menthyldichlorophosphine in 60 ml of TBME is being stirred at −78° C. After addition, stirring is continued at −78° C. for another 1 hour and then without cooling at room temperature for 1.5 hour. After cooling again to −78° C., 19.2 ml (56.6 mmol) of methylmagnesium chloride (3 M solution in THF) are added dropwise within 30 minutes. After addition, stirring is continued first at −78° C. for 10 minutes and then without cooling at room temperature overnight. To the reaction mixture is added dropwise BH$_3$—SMe$_2$ (5.5 ml, 58.0 mmol) and the suspension is stirred at room temperature for 2 hours. Then 100 ml of saturated NaHCO$_3$ solution are added and the mixture is extracted with TBME. The organic phases are collected, dried over sodium sulphate and the solvent is distilled off under reduced pressure on a rotary evaporator. The crude product is obtained as a colourless oil. A $^{31}$P NMR shows that predominantly one of the two possible diastereomeric P-chiral ligands has formed (diastereomer ratio about 5:1). The oil is purified by column chromatography (silica gel 60; eluent=heptane/TBME). A mixture of the two diastereomers is obtained (yield 68%). 1.00 g of the isolated product are suspended in i-propanol (i-PrOH, 3.00 ml) and the mixture is stirred in a water bath at 65° C. for 1 hour. A small amount of the white solid does not go into solution. The suspension is hot-filtered and the filtrate is stirred again at 65° C. for 30 minutes. After 30 minutes, the water bath is switched off and the resulting clear solution is stirred at RT. White crystals precipitate out. The crystals are filtered off and washed with ice-cold i-PrOH (3.00 ml). The diborane adduct B7, optically pure according to NMR, is obtained in the form of colourless crystals (nonoptimized yield 40%).

$^{31}$P NMR (C$_6$D$_6$, 121 MHz): 21.6-22.2 (m, br), 49.2-49.7 (m, br).

b) Preparation of Ligand B7 (HBF$_4$ Salt):

250 mg (0.67 mmol) of the diborane adduct B7, optically pure according to NMR, are suspended in 2 ml of diethylamine (Et$_2$NH) and the resulting mixture is heated to 55° C. in an oil bath. After stirring at 55° C. for 30 minutes, all volatile constituents are distilled off under high vacuum. This operation is repeated five times. To the resulting residue are added 5 ml of diethyl ether (Et$_2$O) and the solvent is drawn off under high vacuum. This operation is repeated twice. The remaining oil is dissolved in 5 ml of diethyl ether and the solution is cooled to 0° C. Then 217 mg (1.34 mmol) of HBF$_4$-Et$_2$O are added dropwise. During the addition, a white solid precipitates out. The cooling bath is removed and the suspension is stirred at room temperature for 30 min. The solid is filtered off and dried under high vacuum. The desired bis-HBF$_4$ salt of ligand B7 is isolated in the form of a white solid in a yield of 82%. The resulting product is converted to a rhodium complex without further analysis.

Example B8

Preparation of the Secondary Phosphine Oxide Ligand B8

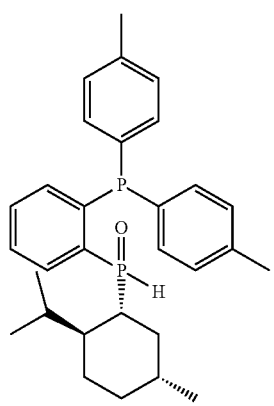

B8

To a solution of 7.87 g (21 mmol) of o-bromophenyldi-para-tolylphosphine in 45 ml of TBME are added dropwise, at −78° C., 14.0 ml (22 mmol) of n-butyllithium (1.6 M in hexane). The resulting suspension is stirred at −78° C. for a further hour, then 5.09 g (21 mmol) of (L)-menthyldichlorophosphine are added. The cooling bath is removed and the temperature allowed to rise to room temperature. 50 ml NaOH 1N are then added and the mixture stirred until the phosphine chloride has been hydrolysed. The reaction mixture is extracted with TBME. The organic phases are collected and dried over sodium sulphate, and the solvent is distilled off under reduced pressure on a rotary evaporator. The crude yield is virtually quantitative. A $^{31}$P NMR of the white solid crude product shows that predominantly one of the two possible diastereomeric P-chiral ligands has formed (diastereomer ratio about 10:1). It is possible by chromatography (silica gel 60; eluent=2:1 heptane/ethyl acetate) to isolate the main stereoisomer in pure form, according to NMR analysis, as a white solid (yield 60%).

$^{31}$P NMR of main diastereomer (C$_6$D$_6$, 121 MHz): δ 16.3 (d), −20.7 (d);

$^1$H NMR of main diastereomer (C$_6$D$_6$, 300 MHz), characteristic signals: δ 8.7-8.6 (m, 1H), 8.67 (dd, J=469.1, 4.7 Hz, 1H), 7.3-6.8 (m, 12H), 2.8-2.7 (m, 1H), 2.2-0.6 (m, 22H)

Example B9 and B9'

Preparation of the Secondary Phosphine Oxide Ligands B9 and B9' (Two Diastereomers)

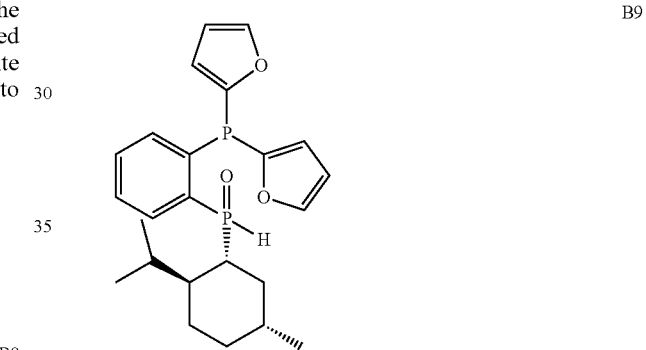

B9

To a solution of 5.3 g (16 mmol) of o-bromophenyl-di-(2-furyl)phosphine in 20 ml of THF are added dropwise, at −78° C., 10.2 ml (16.3 mmol) of n-butyllithium (1.6 M in hexane). The resulting solution is then added via a cannula to a solution of 3.39 g (16.3 mmol) of (L)-menthyldichlorophosphine in 20 ml THF, which is stirred at −78° C. Then the cooling bath is remove and the temperature is allowed to rise to room-temperature. Analysis of a sample of the reaction mixture by $^{31}$P-NMR shows that the reaction is highly diastereoeselective: practically only one of the two possible diastereomers of the phosphinechloride intermediate can be observed: $^{31}$P NMR (C$_6$D$_6$, 121 MHz): δ 105.56 (d), −62.11 (d) J$_{PP}$=248 Hz.

Hydrolysis of this phosphinechloride can lead to two different epimers of the desired product (B8 and B8') which differ in the configuration of the phosphorous of the SPO group.

$^{31}$P NMR (C$_6$D$_6$, 121 MHz) of B9: δ 17.1 (d), −61.4 (d) J$_{PP}$=68 Hz.

$^{31}$P NMR (C$_6$D$_6$, 121 MHz) of B9': δ 31.01 (d), −60.5 (d) J$_{PP}$=58 Hz.

The ratio of B9/B9' can be varied by the choice of the hydrolysis conditions. In each case 2 ml of the reaction mixture with the phosphinechloride intermediate are mixed with 2 ml of the hydrolysis agents described in the following table and the mixture stirred until hydrolysis is complete.

| Hydrolysis conditions | Ratio of B9/B9' * |
|---|---|
| water | 58:42 |
| HCl 1N | 58:42 |
| NaOH 0.5N | 24:76 |
| NaOH 1N | 18:82 |
| NEt$_3$/water 1:4 | 12:88 |

* (based on ratio of the intensisty of the SPO $^{31}$P-NMR signals)

According to $^{31}$P-NMR hydrolysis is quantitative in each case. The two epimers B9 and B9' can be separated (e.g. by chromatography) and isolated in pure form as colorless solids.

Examples B10 and B10'

Preparation of the Secondary Phosphine Oxide Ligands B10 and B10' (Two Diastereomers)

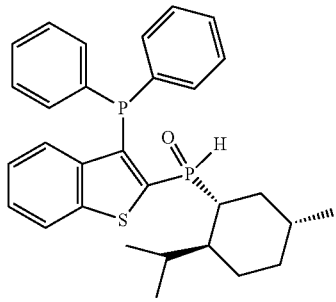

B10

5 ml (8 mmol) n-BuLi (1.6 m in hexane) are added drop wise to a solution of 1.25 ml TMEDA (8.1 mmol) and 2.46 g (7.7 mmol) 3-diphenylphosphine-benzothiophene in THF (15 mL). After stirring for 16 hours, the solution is added to a stirred solution of 1.87 g (7.7 mmol) (L)-menthyl-PCl$_2$ in 10 ml of THF. After 2 hours, the reaction mixture is poured into a mixture of H$_2$O (16 ml) and NEt$_3$ (4 ml) which is stirred at 0° C. After stirring for 2 hours at room temperature, the reaction mixture is extracted with 30 ml of TBME. The organic phases are dried over Na$_2$SO$_4$ and the solvents are distilled off under reduced pressure on a rotary evaporator giving the crude product as a foam (3.8 g) as an approx. 10:1 mixture of two epimers of the desired product (B10 and B10') which differ in the configuration of the phosphorous of the SPO group.

$^{31}$P NMR (C$_6$D$_6$, 121 MHz) of the major epimer B10: δ 27.7 (d), −25.6 (d) J$_{PP}$=67 Hz.

$^{31}$P NMR (C$_6$D$_6$, 121 MHz) of the minor epimer B10': δ 17.8 (d), −27.0 (d) J$_{PP}$=67 Hz. The two epimers are separated e.g. by column chromatography (silica gel 60; eluent=2:1 heptane/ethylacetate) or by crystallization. The major epimer is isolated in good yields in the form of a colourless solid.

$^1$H-NMR of the major epimer B10 (characteristic signals, 300 MHz, C$_6$D$_6$): δ=8.46 (ddd, J$_{PH}$=438. Hz, 1H), 7.6-7.5 (m, 4H), 7.4-7.3 (m, 2H), 7.1-7.0 (m, 6H), 7.0-6.9 (m, 1H), 6.9-6.8 (m, 1H), 3.0-2.9 (m, 1H), 2.5-2.3 (m, 1H), 2.2-2.1 (m, 1H), 2.1-1.9 (m, 1H), 1.04 (d, 3H), 0.83 (d, 3H), 0.63 (d, 3H) 1.6-0.7 (m, 6H).

The following experiments show that the hydrolysis conditions can significantly influence ratio of the epimers of B10 and B10' that are formed:

| hydrolysis agent | ratio B10:B10' | conversion after 30 min. |
|---|---|---|
| H$_2$O/NEt$_3$ 4:1 | 10:1 | complete |
| NaOH 1N | 8:1 | ~95% |
| H$_2$O | 3:1 | ~70% |
| HCl 1N | 1:2 | ~5% |

Examples B11 and B11'

Preparation of the Secondary Phosphine Oxide Ligand B11 and B11' (Two Diastereomers)

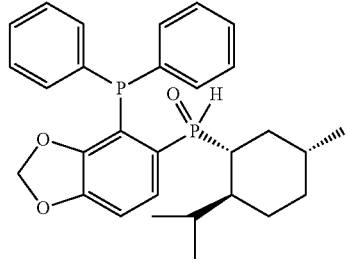

B11

To a solution of 2.0 g (5.19 mmol) of 4-bromo-3-diphenylphosphino-1,2-methylene dioxy)benzene A5 in 5 ml of THF are added dropwise, at −78° C., 3.4 ml (5.4 mmol) of n-butyllithium (1.6 M in hexane). After stirring for 1 hour at the same temperature, 1.3 g (5.2 mmol) of (L)-menthyldichlorophosphine are added. The cooling bath is remove and the mixture is stirred at room temperature over night before it is added to a stirred mixture of 4 ml NEt$_3$ and 25 ml water. After 2 hours, the reaction mixture is extracted with CH$_2$Cl$_2$. The organic phases are collected, dried over Na$_2$SO$_4$ and the solvents are distilled off under reduced pressure on a rotary evaporator giving the crude product as a foam (2.5 g), as an approx. 10:1 mixture of two diastereomers of the desired product.

$^{31}$P NMR (C$_6$D$_6$, 121 MHz) of the major diastereomer B11: δ 17.4 (d), −24.4 (d) J$_{PP}$=74 Hz. $^{31}$P NMR (C$_6$D$_6$, 121 MHz) of the minor diastereomer 11': δ 33.3 (d), −22.4 (d) J$_{PP}$=68 Hz.

The pure major diastereomer B11 is obtained by column chromatography (silica gel 60; eluent=ethylacetate) or recrystallization as a colourless solid (non-optimized yield=40%).

$^1$H-NMR of the major diastereomer B11 (characteristic signals, 300 MHz, C$_6$D$_6$): δ=8.67 (dd, J$_{PH}$=471. Hz, 1H), 8.18 (d, 1H), 7.5-7.0 (div. m, 10H), 6.66 (d, 1H), 4.88 (s, 1H), 4.76 (s, 1H), 2.9-2.7 (m, 1H), 2.4-2.2 (m, 1H), 2.2-2.0 (m, 1H), 1.7-0.6 (div. m, 16H).

Examples B12 and B12'

Preparation of the Phosphine Ligand B12 and B12' (Two Diastereomers)

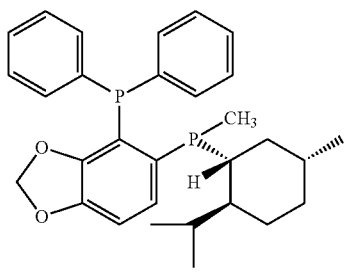

B12

To a solution of 2.0 g (5.19 mmol) of 4-bromo-3-diphenylphosphino-1,2-methylene dioxy)benzene A5 in 5 ml of THF are added dropwise, at −78° C., 3.4 ml (5.4 mmol) of n-butyllithium (1.6 M in hexane). After stirring for 1 hour at the same temperature, 1.3 g (5.2 mmol) of (L)-menthyldichlorophosphine are added. Then the temperature is allowed to rise to room temperature and after 2 hours, 1.77 ml (5.2 mmol) $CH_3MgCl$ (3 M in THF) is added. After 2 hour the mixture is extracted with water, $NH_4Cl$ and $CH_2Cl_2$.

The organic phases are collected, dried over $Na_2SO_4$ and the solvents are distilled off under reduced pressure on a rotary evaporator giving the crude product as a foam (2.5 g). After chromatography, pure B12 is obtained as a colorless solid.

$^{31}P$ NMR ($C_6D_6$, 121 MHz): δ 20.3 (d), −32.4 (d) $J_{PP}$=132 Hz.

$^1$H-NMR (characteristic signals, 300 MHz, $C_6D_6$): δ=7.7-7.5 (m, 3H), 7.25-7.0 (div. m, 8H), 6.72 (m, 1H), 4.95 (s, 1H), 4.90 (s, 1H), 3-0.6 (div. m, 13H), 1.25 (d, 3H), 1.11 (d, 3H), 0.97 (d, 3H).

A small amount of another diastereomer (B12') can also be isolated:

$^{31}P$ NMR ($C_6D_6$, 121 MHz): δ −17.2 (d), −34.6 (d) $J_{PP}$=146 Hz.

Examples B13 and B13'

Preparation of the Secondary Phosphine Oxide Ligand B13 and B13' (Two Diastereomers

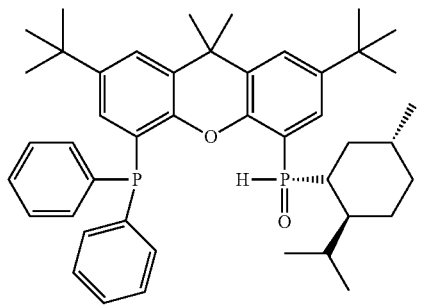

B13

To a solution of 0.35 g (0.59 mmol) of 4-bromo-5-diphenylphosphino-2,7-di-tert-butyl-9,9-dimethylxanthene in 2 ml of THF are added dropwise, at −78° C., 0.38 ml (0.61 mmol) of n-butyllithium (1.6 M in hexane). After stirring for 1 hour at the same temperature, this solution is added to 0.143 g (0.59 mmol) of (L)-menthyldichlorophosphine in 0.5 ml THF which is stirred at −78° C. The temperature is then allowed to rise to room temperature and, after stirring for 1 hour, the mixture is added to a stirred solution of 4 ml water and 0.4 ml $NEt_3$. After 2 hour the mixture is extracted with $CH_2Cl_2$. The organic phases are collected, dried over $Na_2SO_4$ and the solvents are distilled off under reduced pressure on a rotary evaporator giving the crude product as a foam. This foam contains a major epimer B12 and a minor epimer B12', which differ in the configuration of the phosphorous of the SPO group (ratio of major/minor epimer=approx. 2:1. These epimers can be separated and purified by chromatography.

$^{31}P$ NMR ($C_6D_6$, 121 MHz) of the major epimer B13: δ 24.5 (d), −14.0 (d) $J_{PP}$=~6 Hz.

$^{31}P$ NMR ($C_6D_6$, 121 MHz) of the minor epimer B13': δ 17.7 (d), −16.0 (d) $J_{PP}$=~9 Hz.

Examples B14 and B14'

Preparation of the Secondary Phosphine Oxide Ligand B14 and B14' (Two Diastereomers)

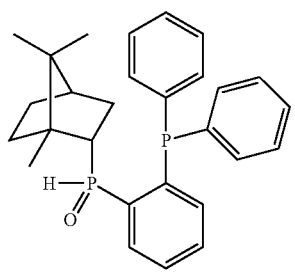

B14

1-Bromo-2-diphenylphosphinoylbenzene (272 mg, 0.866 mmol) is dissolved in THF (5 mL) and cooled to −78° C. n-Butyllithium (1.6 M in hexane, 0.55 mL, 0.880 mmol) was added dropwise and stirred for 1 hour to give an orange solution which is then transferred via cannula to a solution of 207 mg (0.866 mmol) dichloro(1R-2S-4R-1,7,7-trimethyl-bicyclo[2.2.1]heptan-2-yl)phosphine A6 in 5 ml THF at −78° C. After 15 min the reaction mixture is allowed to warm up to room temperature and dropped into a solution of 2 ml $NEt_3$ and 8 ml water. The mixture is extracted with ethylacetate and sat. aq. $NaHCO_3$. The organic phases are washed with sat. aq. NaCl and dried over $MgSO_4$. After evaporation of the solvent the crude product is purified by column chromatography ($SiO_2$, hexane:EtOAc (1:1)) to give the two diastereoisomers of the title compound (major diastereomer B14 (125 mg) and minor diastereomer B14' (90 mg), total yield=56%) as white foams.

Major Diastereoisomer B14:

$^{31}P$-NMR ($C_6D_6$): δ=9.9 (d), −23.2 (d), $J_{PP}$=72 Hz.

$^1$H-NMR ($C_6D_6$): δ=0.24 (s, 3H), 0.68 (s, 3H), 1.03 (s, 3H), 1.30-1.46 (m, 2H), 1.49 (t, 1H), 1.61-1.76 (m, 2H), 1.96 (m, 1H), 2.13-2.20 (m, 1H), 2.92 (m, 1H), 6.94 (t, 1H), 6.96-7.03

(m, 6H), 7.04-7.08 (m, 1H), 7.08-7.15 (m, 5H), 8.48-8.56 (m, 1H), 8.68 (dd, $J_{PH}$=470 Hz, $J_{HH}$=4.5 Hz, 1H).

Minor Diastereomer B14':

$^{31}$P-NMR (C$_6$D$_6$): δ=24.7 (d), −19.8 (d), $J_{PP}$=52 Hz.

$^1$H-NMR (C$_6$D$_6$): δ=0.54 (s, 3H), 0.66 (s, 3H), 1.00 (s, 3H), 1.27-1.36 (m, 1H), 1.32-1.46 (m, 1H), 1.40-1.50 (m, 1H), 1.41-1.45 (m, 1H), 1.54-1.68 (m, 2H), 2.56 (m, 1H), 2.68-2.78 (m, 1H), 6.83 (t, 1H), 6.97-7.06 (m, 7H), 7.00-7.06 (m, 1H), 7.15-7.25 (m, 2H), 7.32-7.37 (m, 2H), 8.03 (m, 1H), 8.22 (dt, $J_{PH}$=466 Hz, J=4.5 Hz, 1H).

C) PREPARATION OF METAL COMPLEXES

Example C1

Preparation of Rh Complex C1 with Ligand B7

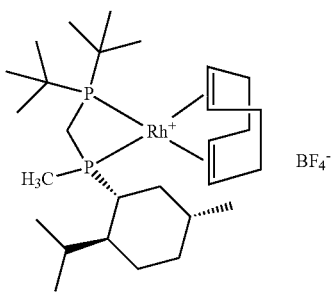

C1

To a solution of 170 mg (0.548 mmol) of Rh(cod)acac in 2 ml of THF (2.00 ml) are added in portions, at 0° C. with stirring within 20 minutes, 285 mg (0.548 mmol) of ligand B7 (HBF$_4$ salt). The initially orange solution turns dark red during the addition. The mixture is stirred at 0° C. for 1 hour, the cooling bath is removed and the mixture is stirred at room temperature for another 1 hour. After the solvent has been drawn off under high vacuum, a red-brown oil is obtained. This is stirred in 5 ml of diethyl ether for approx. 10 minutes. This forms a solid. After stirring for a further 20 minutes, the solid is filtered off, washed twice with 5 ml each time of diethyl ether and dried under high vacuum. The solid is dissolved again in 10 ml of CHCl$_3$, the solution is filtered through Hyflo, the solvent is distilled off and the remaining solid is dried under high vacuum. The desired Rh complex is obtained in the form of an orange solid in a yield of 77%.

$^{31}$P NMR (CDCl$_3$, 121 MHz): −4.9 (dd, J=134 Hz, J=61 Hz), −45.7 (dd, J=122 Hz, J=61 Hz).

The following complexes are prepared by the following method:

The Rh or Ir complexes are prepared by mixing 1 equivalent of ligand with 0.95 molar equivalent of [Rh(nbd)$_2$]BF$_4$ or [Ir(cod)$_2$]BF$_4$, in methanol or CD$_3$OD. In general, the complex is formed within less than 10 minutes. The solutions are analysed directly by means of $^{31}$P NMR. The complexes can be isolated by precipitation with, for example, heptane and, if desired, be purified by recrystallization.

Example C2

Complex C2 ([Rh(nbd)$_2$]BF$_4$ with Ligand B6)

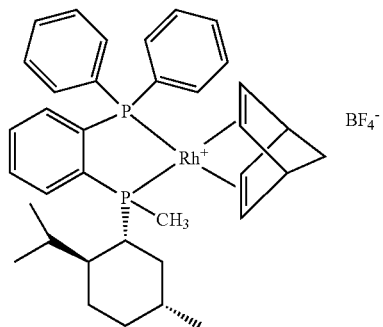

C2

$^{31}$P NMR (CD$_3$OD, 121 MHz): δ 59.03 (dd, J=159 Hz, J=27.4 Hz), 51.1 (dd, J=151 Hz, J=27.4 Hz)

Example C3

Complex C3 ([Rh(nbd)$_2$]BF$_4$ with Ligand B2)

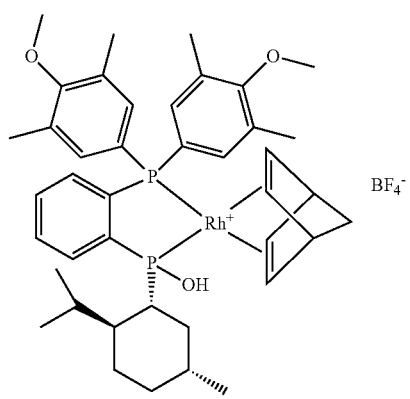

B2

$^{31}$P NMR (CD$_3$OD, 121 MHz): δ 143.5 (dd, J=174 Hz, J=27.8 Hz), 54.4 (dd, J=167 Hz, J=27.8 Hz)

Example C4

Complex C4 ([Rh(nbd)₂]BF₄ with Ligand B3)

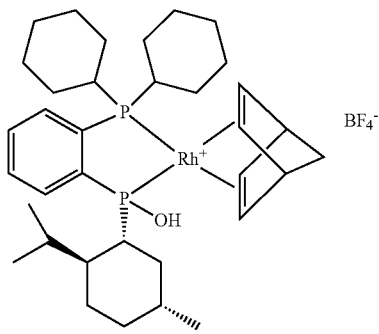

³¹P NMR (CD₃OD, 121 MHz): δ 137.2 (dd, J=178 Hz, J=26.8 Hz), 67.3 (dd, J=159.2 Hz, J=26.8 Hz)

Example C5

Complex C5 ([Ir(cod)₂]BF₄ with Ligand B3)

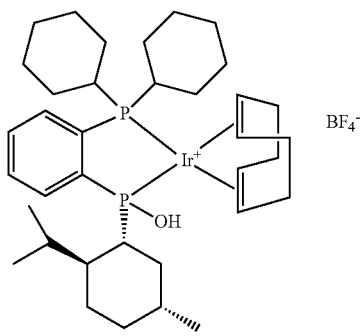

³¹P NMR (CD₃OD, 121 MHz): δ 121.9 (d, J=8.0 Hz), 56.0 (d, J=8.0 Hz)

Example C6

Complex C6 ([Rh(nbd)₂]BF₄ with Ligand B4)

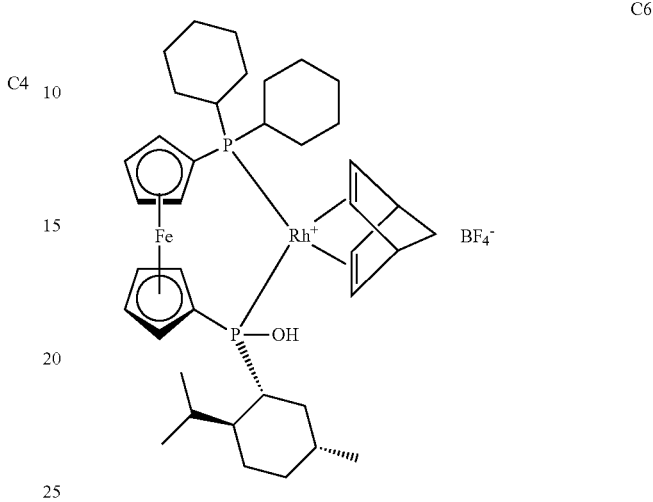

This complex forms only very slowly (reaction solution is stirred overnight). ³¹P NMR (CD₃OD, 121 MHz): δ 120.4 (dd, J=181 Hz, J=30 Hz), 31.2 (dd, J=158 Hz, J=30 Hz)

D) APPLICATION EXAMPLES

As described in the experimental part—unless stated otherwise—the ligands used below are optically pure according to NMR analysis. The detection limit for another diastereomer in this analysis method is about ≧3-4%. It is thus possible that a further purification of the ligands or metal complexes used, for example by recrystallization, may lead to even purer ligands and hence to even higher enantioselectivities in the following hydrogenation examples.

Examples D1-D43

Hydrogenation of Various Unsaturated Substrates

All operations are performed under argon and with degassed solvents. The hydrogenations are carried out in glass vials (low hydrogen pressure) or in steel autoclaves (high hydrogen pressure). Agitation is effected either by a magnetic stirrer or by shaking the reactor. The catalysts are prepared 'in situ' by mixing 1 mol-equivalent of a metal of a metal precursor (see table 2) with 1.1 mol-equivalents of ligand in the solvent given in table 2. The substrate is dissolved in the solvent given in table 2 and added to the catalyst as a solution. Subsequently, the inert gas is exchanged for hydrogen and the hydrogenation is started by starting agitation.

TABLE 1

Substrates

| Substrate | Structures | | Determination of conversion and ee |
|---|---|---|---|
| DMI | CH₂=C(COOMe)CH₂COOMe → CH₃CH(COOMe)CH₂COOMe (H₂) | | GC with chiral column: Lipodex-E |

TABLE 1-continued

Substrates

| Substrate | Structures | Determination of conversion and ee |
|---|---|---|
| MAA | CH$_2$=C(COOCH$_3$)(NHCOCH$_3$) →$^{H_2}$ CH$_3$-CH(COOCH$_3$)(NHCOCH$_3$) | GC with chiral column: Chirasil-L-val |
| MAC | PhCH=C(COOMe)(NHCOCH$_3$) →$^{H_2}$ PhCH$_2$-CH(COOMe)(NHCOCH$_3$) | GC with chiral column: Chirasil-L-val |
| ACA | PhCH=C(COOH)(NHCOCH$_3$) →$^{H_2}$ PhCH$_2$-CH(COOH)(NHCOCH$_3$) | First derivatization with TMS-diazomethane, then GC with chiral column: Chirasil-L-val |
| Z-EAAC | (Z)-CH$_3$C(NHAc)=CHCOOEt →$^{H_2}$ CH$_3$CH(NHAc)CH$_2$COOEt | GC with chiral column: Betadex-110 |
| E-EAAC | (E)-CH$_3$C(NHAc)=CHCOOEt →$^{H_2}$ CH$_3$CH(NHAc)CH$_2$COOEt | GC with chiral column: Betadex-110 |
| EOP | CH$_3$CH$_2$COCH$_2$COOEt →$^{H_2}$ CH$_3$CH$_2$CH(OH)CH$_2$COOEt | GC with chiral column: Lipodex-E |
| EBA | PhCOCH$_2$COOEt →$^{H_2}$ PhCH(OH)CH$_2$COOEt | HPLC with chiral column: Chiracel-OD-H |
| ETAA | F$_3$CCOCH$_2$COOEt →$^{H_2}$ F$_3$CCH(OH)CH$_2$COOEt | GC with chiral column: Lipodex-E |

The abbreviations in Table 1 mean: ee=enantiomeric excess, GC=gas chromatography, TMS=trimethylsilyl, HPLC=high-pressure liquid chromatography.

TABLE 2

Hydrogenation results

| No. | Lig. | Metal | Substrate | [S] | S/C | Sol. | P | T | t [h] | C (%) | ee (%) |
|---|---|---|---|---|---|---|---|---|---|---|---|
| D1 | B1 | Rh[a)] | MAA | 0.25 | 200 | MeOH | 1 | 25 | 1 | 100 | −96.4 |
| D2 | B1' | Rh[a)] | MAA | 0.25 | 200 | MeOH | 1 | 25 | 1 | 100 | 83.3 |
| D3 | B2 | Rh[a)] | MAA | 0.25 | 200 | MeOH | 1 | 25 | 1 | 100 | −99.1 |
| D4 | B2 | Rh[a)] | MAC | 0.25 | 200 | MeOH | 1 | 25 | 1 | 50 | −93.3 |
| D5 | B1 | Ir[c)] | EOP | 0.1 | 25 | DCE | 80 | 80 | 14 | 62 | 74.6 |
| D6 | B1 | Rh[a)] | EOP | 0.36 | 100 | THF | 80 | 80 | 14 | 95 | −47.2 |
| D7 | B1 | Ir[c)] | ETAA | 0.36 | 100 | DCE | 80 | 80 | 14 | 100 | −72.8 |
| D8 | B1 | Ir[c)] | EBA | 0.36 | 100 | DCE | 80 | 80 | 14 | 100 | −89.1 |
| D9 | B3 | Rh[a)] | MAA | 0.25 | 370 | MeOH | 1 | 25 | <0.1 | 100 | −96.4 |
| D10 | B3 | Rh[a)] | MAC | 0.25 | 200 | MeOH | 1 | 25 | 1 | 100 | −94.0 |
| D11 | B3 | Rh[a)] | ACA | 0.25 | 200 | MeOH | 1 | 25 | 1 | 100 | −97.0 |
| D12 | B4 | Rh[a)] | MAA | 0.25 | 200 | MeOH | 1 | 25 | 1 | 100 | −57 |
| D13 | B4' | Rh[a)] | MAA | 0.25 | 200 | MeOH | 1 | 25 | 1 | 100 | 47 |
| D14 | B5 | Rh[a)] | MAA | 0.25 | 200 | MeOH | 1 | 25 | 1 | 100 | 69 |
| D15 | B8 | Rh[a)] | MAA | 0.25 | 200 | MeOH | 1 | 25 | <0.1 | 100 | −98.4 |
| D16 | B8 | Rh[a)] | DMI | 0.25 | 200 | MeOH | 1 | 25 | <0.1 | 100 | −98.5 |
| D17 | B8 | Rh[a)] | MAC | 0.36 | 100 | EtOH | 1 | 25 | 2 | 100 | −95.6 |
| D18[1)] | B8 | Rh[d)] | ACA | 0.36 | 100 | DCE | 1 | 25 | 2 | 100 | −99.2 |
| D19 | B8 | Rh[a)] | E-EAAC | 0.36 | 100 | THF | 1 | 25 | 2 | 100 | 94.0 |
| D20 | B8 | Rh[a)] | Z-EAAC | 0.36 | 100 | EtOH(9) TFE(1) | 1 | 25 | 2 | 100 | 67.7 |
| D21 | B8 | Ir[c)] | ETAA | 0.36 | 100 | DCE | 80 | 80 | 14 | 100 | −72.9 |
| D22 | B8 | Ir[c)] | EBA | 0.36 | 100 | DCE | 80 | 80 | 14 | 92 | −86.7 |
| D23 | B8 | Rh[a)] | EBA | 0.36 | 100 | THF | 80 | 80 | 14 | 100 | 47.6 |
| D24 | B8 | Ru[b)] | EBA | 0.1 | 25 | EtOH | 80 | 80 | 14 | 57 | −48.4 |
| D25 | B10 | Rh[a)] | MAA | 0.25 | 200 | MeOH | 1 | 25 | 1 | 100 | 99.8 |
| D26[1)] | B10 | Rh[a)] | ACA | 0.36 | 100 | EtOH | 1 | 25 | 2 | 100 | >99.5 |
| D27 | B10 | Rh[a)] | MAC | 0.25 | 200 | MeOH | 1 | 25 | 1 | 100 | 98.7 |
| D28 | B10 | Rh[a)] | DMI | 0.25 | 200 | MeOH | 1 | 25 | 1 | 100 | >99.5 |
| D29 | B10 | Rh[a)] | E-EAAC | 0.36 | 100 | EtOH | 1 | 25 | 2 | 100 | −97.3 |
| D30 | B10 | Rh[a)] | Z-EAAC | 0.36 | 100 | EtOH(9) TFE(1) | 1 | 25 | 2 | 100 | −75.6 |
| D31 | B10 | Ru[b)] | ETAA | 0.1 | 25 | DCE | 80 | 80 | 14 | 100 | −72.4 |
| D32 | B10 | Ir[c)] | EBA | 0.36 | 100 | DCE | 80 | 80 | 14 | >95 | 68.7 |
| D33 | B10 | Rh[a)] | EBA | 0.0.1 | 25 | THF | 80 | 80 | 14 | 100 | −51.8 |
| D34 | B10 | Rh[a)] | EOP | 0.36 | 100 | THF | 80 | 80 | 14 | >90 | 45.7 |
| D35 | B11 | Rh[a)] | MAA | 0.25 | 200 | MeOH | 1 | 25 | 1 | 100 | −96 |
| D36 | B14 | Rh[a)] | MAA | 0.25 | 200 | MeOH | 1 | 25 | 1 | 100 | −77.5 |
| D37 | B14 | Rh[a)] | DMI | 0.25 | 200 | MeOH | 1 | 25 | 1 | 100 | −77.3 |
| D38 | B14' | Rh[a)] | MAA | 0.25 | 200 | MeOH | 1 | 25 | 1 | 100 | 92.7 |
| D39 | B14' | Rh[a)] | DMI | 0.25 | 200 | MeOH | 1 | 25 | 1 | 100 | 90.1 |
| D40 | B6 | Rh[a)] | MAA | 0.25 | 200 | MeOH | 1 | 25 | 1 | 100 | −97 |
| D41 | B7 | Rh[a)] | MAA | 0.25 | 200 | MeOH | 1 | 25 | 1 | 100 | 95 |
| D42 | B7 | Rh[a)] | MAC | 0.25 | 200 | MeOH | 1 | 25 | 1 | 50 | 97.2 |
| D43 | B12 | Rh[a)] | MAA | 0.25 | 200 | MeOH | 1 | 25 | 1 | 100 | −92 |

Additions: [1)]12 mol-equivalents of 1,4-diazobicyclo[2.2.2]octane/metal;

In the table 2: [S] means molar substrate concentration; S/C means substrate/catalyst ratio; t means hydrogenation time (in most cases, the time needed to obtain complete conversion is shorter); Lig. means ligand, Sol. means solvent (MeOH=methanol; EtOH=ethanol; Tol=toluene; THF=tetrahydrofuran; DCE=1,2-dichloroethane, TFE=2,2,2-Trifluoroethanol);

Metal means metal precursor which is used in the hydrogenations:

Rh[a)]=[Rh(norbornadiene)$_2$]BF$_4$; Ru[b)]=[RuI$_2$(p-methylcumene)]$_2$;

[Ir[c)]=[Ir(cyclooctadiene)Cl]$_2$; Rh[d)]=[Rh(norbornadiene)Cl]$_2$.

C=conversion; ee=enantiomeric excess of the hydrogenation product. A positive number means that the GC or HPLC peak of the enantiomer with the shorter retention time is larger than that of the enantiomer with the longer retention time, a negative number means that the GC or HPLC peak of the enantiomer with the longer retention time is larger than that of the enantiomer with the shorter retention time.

The invention claimed is:

1. Compounds of the formula (I) in the form of a mixture of predominantly one diastereomer or in the form of a mixture of pure diastereomers, $$Z_1\text{-Q-P*}R_0R_1 \quad (I),$$

wherein:

$Z_1$ is a C-bonded, secondary phosphine group of the formula —P(R)$_2$, wherein R is a hydrocarbon radical or O-atom(s)-containing heterohydrocarbon radical having 1 to 18 carbon atoms and optionally substituted by $C_1$-$C_6$-alkyl, trifluoromethyl, $C_1$-$C_6$-alkoxy, trifluoromethoxy, $(C_1$-$C_4$-alkyl)$_2$amino, $(C_6H_5)_3$Si, $(C_1$-$C_{12}$-alkyl)$_3$Si or halogen;

Q is selected from the group consisting of:
(i) an optionally substituted achiral aromatic group, wherein the achiral aromatic group is bonded directly to $Z_1$ through a carbon atom of the achiral aromatic group, or optionally bonded to $Z_1$ through a $C_1$-$C_4$-alkylene group, and bonded directly to $P^*R_0R_1$ through a carbon atom of the achiral aromatic group, or optionally bonded to $P^*R_0R_1$ through a $C_1$-$C_4$-alkylene group, which is optionally interrupted by a heteroatom selected from the group consisting of O, S, N, Fe and Si, (ii) an optionally substituted achiral ferrocene group, wherein the achiral ferrocene group is bonded directly to $Z_1$ through a carbon atom of the achiral ferrocene group, or optionally bonded to $Z_1$ through a $C_1$-$C_4$-alkylene group, and bonded directly to $P^*R_0R_1$ through a carbon atom of the achiral ferrocene group, or optionally bonded to $P^*R_0R_1$ through a $C_1$-$C_4$-alkylene group, which is optionally interrupted by a heteroatom selected from the group consisting of O, S, N, Fe and Si, (iii) an optionally substituted cycloalkane or heterocycloalkane group, wherein the cycloalkane or heterocycloalkane group is bonded directly to $Z_1$ through a carbon atom of the cycloalkane or heterocycloalkane group, or optionally bonded to $Z_1$ through a $C_1$-$C_4$-alkylene group, and bonded directly to $P^*R_0R_1$ through a carbon atom of the cycloalkane or heterocycloalkane group, or optionally bonded to $P^*R_0R_1$ through a $C_1$-$C_4$-alkylene group, which is optionally interrupted by a heteroatom selected from the group consisting of O, S, N, Fe, and Si, and (iv) an optionally substituted $C_1$-$C_4$-alkylene group;

P* is a chiral phosphorus atom;

$R_0$ is hydroxyl; and $R_1$ is a C-bonded optically enriched or optically pure chiral, mono- or polycyclic, nonaromatic hydrocarbon ring, or tautomers thereof.

2. The compounds according to claim 1, wherein the secondary phosphine $Z_1$ is selected from the group consisting of: —P($C_1$-$C_6$-alkyl)$_2$, —P($C_5$-$C_8$-cycloalkyl)$_2$, —P(o-furyl)$_2$, —P($C_6H_5$)$_2$, —P[2-($C_1$-$C_6$-alkyl)$C_6H_4$]$_2$, —P[3-($C_1$-$C_6$-alkyl)$C_6H_4$]$_2$, —P[4-($C_1$-$C_6$-alkyl)$C_6H_4$]$_2$, —P[2-($C_1$-$C_6$-alkoxy)$C_6H_4$]$_2$, —P[3-($C_1$-$C_6$-alkoxy)$C_6H_4$]$_2$, —P[4-($C_1$-$C_6$-alkoxy)$C_6H_4$]$_2$, —P[2-(trifluoromethyl)$C_6H_4$]$_2$, —P[3-(trifluoromethyl)$C_6H_4$]$_2$, —P[4-(trifluoromethyl)$C_6H_4$]$_2$, —P[3,5-bis(trifluoromethyl)$C_6H_3$]$_2$, —P[3,5-bis($C_1$-$C_6$-alkyl)$_2C_6H_3$]$_2$, —P[3,5-bis($C_1$-$C_6$-alkoxy)$_2C_6H_3$]$_2$ and —P[3,5-bis($C_1$-$C_6$-alkyl)$_2$-4-($C_1$-$C_6$-alkoxy)$C_6H_2$]$_2$.

3. The compounds according to claim 1, wherein the phosphorus atoms are linked via a carbon chain having 1 to 4 carbon atoms or via a —C—Fe—C— group.

4. The compounds according to claim 1, wherein Q is (a) a group of the formula

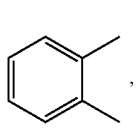 , 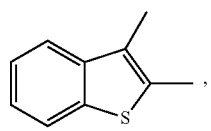 ,

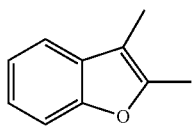 , or 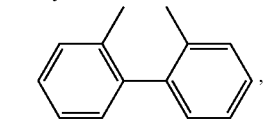 , (b) 1,1'-biaryl-2,2'-diyl of the formula

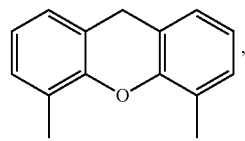 [SMILES: Cc1cccc2c1Oc1c(C)cccc1C2] , (c) 1,1'-ferrocenylene of the formula

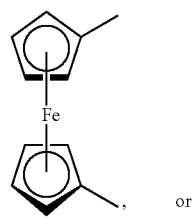 , or (d) a linear $C_1$-$C_4$-alkylene, wherein each of (a), (b), (c) and (d) are independently optionally substituted.

5. The compounds according to claim 1, wherein Q is an unsubstituted or substituted group of the formula

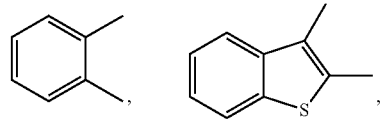 or

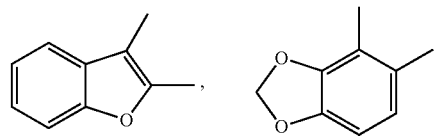

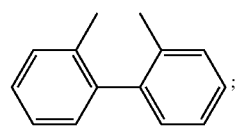 ;

and $R_1$ is menthyl, bornyl or isopinocamphyl.

6. The compounds according to claim 1, wherein Q is an unsubstituted or substituted group of the formula

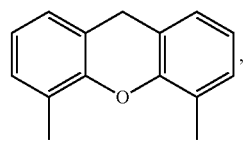 [SMILES: Cc1cccc2c1Oc1c(C)cccc1C2] , and $R_1$ is menthyl, bornyl or isopinocamphyl.

7. The compounds according to claim 1, wherein Q is unsubstituted 1,1'-ferrocenylene of the formula

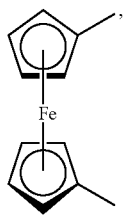

and $R_1$ is menthyl, bornyl or isopinocamphyl.

8. The compounds according to claim 1, wherein Q is unsubstituted or $C_1$-$C_4$-alkyl-substituted $C_1$-$C_4$-alkylene.

9. The compounds according to claim 8, wherein Q is unsubstituted $C_1$-$C_4$-alkylene;

and $R_1$ is menthyl, bornyl or isopinocamphyl.

10. The compounds according to claim 1, wherein Q is selected from the group consisting of methylene and a group of the formula

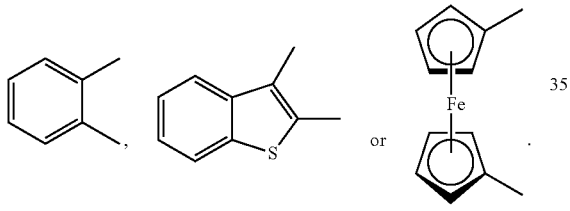

11. The compounds according to claim 1, wherein $R_1$ is a mono- or polycyclic hydrocarbon ring bonded to the phosphorus atom represented by the formula

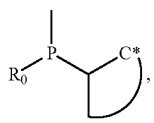

wherein C* is a stereogenic carbon atom in the α position to the P—C bond, the "arc" with the bonds represents the mono- or polycyclic ring, and C* has a substituent and is part of the ring.

12. The compounds according to claim 1, wherein $R_1$ is a terpene.

13. The compounds according to claim 12, wherein the terpene is selected from the group consisting of menthyl, bornyl and isopinocamphyl.

14. The compounds according to claim 12, wherein $R^1$ is selected from the group consisting of

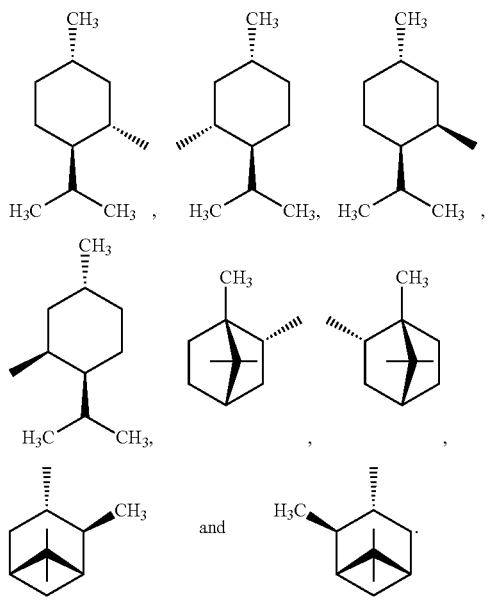

15. The compounds according to claim 1, wherein the compounds are both enantiomers of a compound represented by a formula selected from the group consisting of 51
-continued
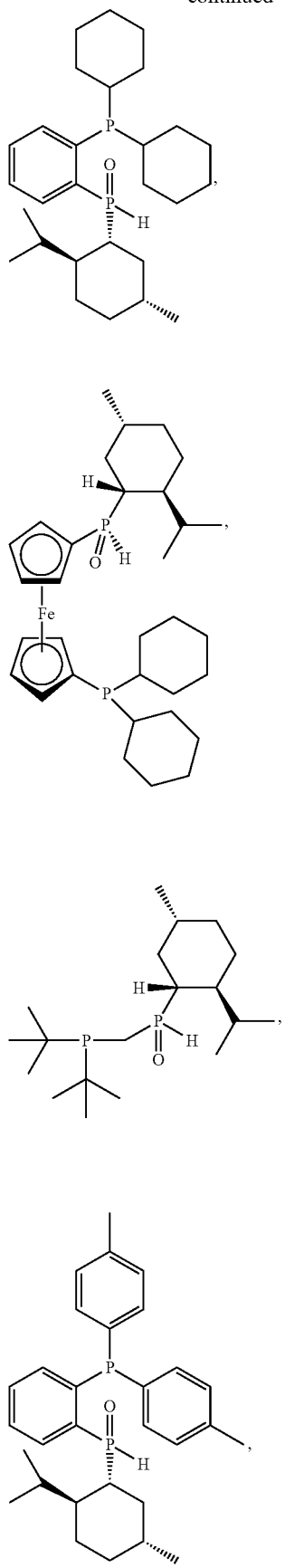
52
-continued
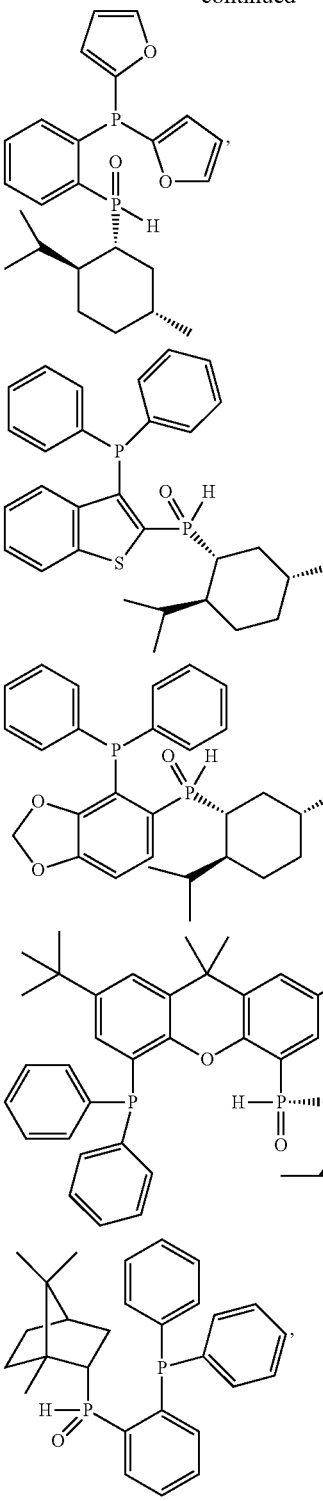
wherein the stereogenic phosphorus has an absolute configuration of R or S.
16. A process for preparing the compounds of formula (I) according to claim 1, comprising:
reacting a compound of the formula (II),
secondary phosphine-Q-Hal   (II), wherein the secondary phosphine is a group of the formula —P(R)$_2$, wherein R is as defined in claim 1, Q is as defined in claim 1, and Hal is Cl, Br or I, with a metallating reagent to obtain an intermediate, and then reacting the intermediate with a halophosphine of the formula (IIIa) or the formula (IIIb), Hal$_1$-PX$_3$R$_1$            (IIIa)

(Hal$_1$)$_2$PR$_1$            (IIIb), wherein:
R$_1$ is as defined in formula (I) of claim 1,
Hal$_1$ is Cl, Br or I, and
X$_3$ is C$_1$-C$_4$-alkoxy, C$_5$-C$_7$-cycloalkoxy or (C$_1$-C$_4$-alkyl)$_2$amino,
to form a compound of the formula (IVa) or the formula (IVb), secondary phosphine-Q-P(Hal$_1$)R$_1$            (IVa)

secondary phosphine-Q-P(X$_3$)R$_1$            (IVb), wherein secondary phosphine, Q, Hal$_1$, R$_1$ and X$_3$ are as defined above,
and then either;
(1) hydrolyzing the compound of the formula (IVa) or the formula (IVb) by
mixing a reaction mixture comprising the compound of the formula (IVa) or the formula (IVb) with water,
mixing a reaction mixture comprising the compound of the formula (IVa) or the formula (IVb) with water containing an acid, or
mixing a reaction mixture comprising the compound of the formula (IVa) or the formula (IVb) with water containing a base,
wherein the reaction mixture is obtained by adding a hydrolyzing medium to the compound of the formula (IVa) or the formula (IVb), or by adding the compound of the formula (IVa) or the formula (IVb) to the hydrolyzing medium, or
(2) reacting a compound of formula (IVa) with a primary amine, a secondary amine or an alcohol to form an aminophosphine or a phosphinite,
and then hydrolyzing the aminophosphine or phosphinite by
mixing a reaction mixture comprising the aminophosphine or phosphinite with water,
mixing a reaction mixture comprising aminophosphine or phosphinite with water containing an acid,
mixing a reaction mixture comprising the aminophosphine or phosphinite with water containing a base, or
reacting the aminophosphine or phosphinite with a carboxylic acid to obtain the compounds of formula (I).

17. A metal complex of transition metals of the transition groups of the Periodic Table of the Elements with a compound according to claim 1 as a ligand.

18. A process for preparing the compounds of formula (I) according to claim 1, comprising:
reacting a compound of the formula (II'), secondary phosphine-Q-active hydrogen            (II'), wherein the secondary phosphine is a group of the formula —P(R)$_2$, R is as defined in claim 1 and Q is as defined in claim 1, with a metallating reagent to obtain an intermediate, and then reacting the intermediate with a halophosphine of the formula (IIIa) or the formula (IIIb), Hal$_1$-PX$_3$R$_1$            (IIIa)

(Hal$_1$)$_2$PR$_1$            (IIIb), wherein:
R$_1$ is as defined in formula (I) of claim 1,
Hal$_1$ is Cl, Br or I, and
X$_3$ is C$_1$-C$_4$-alkoxy, C$_5$-C$_7$-cycloalkoxy or (C$_1$-C$_4$-alkyl)$_2$-amino,
to form a compound of the formula (IVa) or the formula (IVb), secondary phosphine-Q-P(Hal$_1$)R$_1$            (IVa)

secondary phosphine-Q-P(X$_3$)R$_1$            (IVb), wherein secondary phosphine, Q, Hal$_1$, R$_1$ and X$_3$ are as defined above,
and then either:
(1) hydrolyzing the compound of the formula (IVa) or the formula (IVb) by
mixing a reaction mixture comprising the compound of the formula (IVa) or the formula (IVb) with water,
mixing a reaction mixture comprising the compound of the formula (IVa) or the formula (IVb) with water containing an acid, or
mixing a reaction mixture comprising the compound of the formula (IVa) or the formula (IVb) with water containing a base,
wherein the reaction mixture is obtained by adding a hydrolyzing medium to the compound of the formula (IVa) or the formula (IVb), or by adding the compound of the formula (IVa) or the formula (IVb) to the hydrolyzing medium, or
(2) reacting a compound of formula (IVa) with a primary amine, a secondary amine or an alcohol to form an aminophosphine or a phosphinite,
and then hydrolyzing the aminophosphine or phosphinite by
mixing a reaction mixture comprising the aminophosphine or phosphinite with water,
mixing a reaction mixture comprising aminophosphine or phosphinite with water containing an acid,
mixing a reaction mixture comprising the aminophosphine or phosphinite with water containing a base, or
reacting the aminophosphine or phosphinite with a carboxylic acid to obtain the compounds of formula (I).

\* \* \* \* \*

UNITED STATES PATENT AND TRADEMARK OFFICE
CERTIFICATE OF CORRECTION

PATENT NO. : 8,450,501 B2  
APPLICATION NO. : 12/734696  
DATED : May 28, 2013  
INVENTOR(S) : Benoit Pugin Page 1 of 1

It is certified that error appears in the above-identified patent and that said Letters Patent is hereby corrected as shown below:

In the Claims:

Claim 14, in column 50, line 1:

"wherein $R^1$", should read

--wherein $R_1$--.

Signed and Sealed this  
Sixth Day of August, 2013

Teresa Stanek Rea  
*Acting Director of the United States Patent and Trademark Office*